US012605521B2

(12) United States Patent
Lin

(10) Patent No.: US 12,605,521 B2
(45) Date of Patent: Apr. 21, 2026

(54) BREATHING EQUIPMENT FOR PROVIDING POSITIVE PRESSURE GAS

(71) Applicant: Hsin-Yung Lin, Taoyuan (TW)

(72) Inventor: Hsin-Yung Lin, Taoyuan (TW)

( * ) Notice: Subject to any disclaimer, the term of this patent is extended or adjusted under 35 U.S.C. 154(b) by 1111 days.

(21) Appl. No.: 17/630,708

(22) PCT Filed: Jun. 23, 2020

(86) PCT No.: PCT/CN2020/097612
§ 371 (c)(1),
(2) Date: Jan. 27, 2022

(87) PCT Pub. No.: WO2021/022921
PCT Pub. Date: Feb. 11, 2021

(65) Prior Publication Data
US 2022/0257899 A1     Aug. 18, 2022

(30) Foreign Application Priority Data

Aug. 6, 2019     (CN) .......................... 201910720008.8

(51) Int. Cl.
*A61M 16/16*        (2006.01)
*A61M 16/00*        (2006.01)
*C25B 1/04*         (2021.01)

(52) U.S. Cl.
CPC ........ *A61M 16/16* (2013.01); *A61M 16/0003* (2014.02); *C25B 1/04* (2013.01);
(Continued)

(58) Field of Classification Search
CPC ...... A61M 16/16; A61M 16/14; A61M 16/10; A61M 16/00; A61M 16/0003;
(Continued)

(56) References Cited

U.S. PATENT DOCUMENTS 4,589,409  A  *  5/1986  Chatburn .......... A61M 16/1075
                                                  128/203.26
6,041,777  A      3/2000  Faithfull
                          (Continued)

FOREIGN PATENT DOCUMENTS

CN            1519393  A      8/2004
CN          104867025  A      8/2015
                          (Continued)

OTHER PUBLICATIONS

Machine translation of CN108411327A of description and claims using google patents (Year: 2018).*
(Continued)

*Primary Examiner* — Bradley H Philips
*Assistant Examiner* — Tyler A Raubenstraw
(74) *Attorney, Agent, or Firm* — Rosenberg, Klein & Lee

(57)          ABSTRACT

A breathing equipment for providing a positive pressure gas includes a gas channel, a hydrogen generating device, a pressurizing device, a mixing device, an atomizing device, and an output device. The hydrogen generating device, the pressurizing device, the mixing device, the atomizing device, and the output device are all coupled to the gas channel. The hydrogen generating device is configured to electrolyze water to generate a gas comprising hydrogen. The pressurizing device selectively accelerates an external gas to generate an accelerating gas. The mixing device is configured to mix the gas comprising hydrogen and the accelerating gas to generate a positive pressure gas. The atomizing device is configured to selectively generate an atomizing gas. The output device is configured to selectively output the gas comprising hydrogen, the positive pressure gas, the gas comprising hydrogen with the atomizing gas, or the positive pressure gas with the atomizing gas.

18 Claims, 16 Drawing Sheets

(52) U.S. Cl.
    CPC ............... *A61M 2016/0027* (2013.01); *A61M 2016/003* (2013.01); *A61M 2205/3334* (2013.01); *A61M 2205/75* (2013.01)

(58) Field of Classification Search
    CPC .......... A61M 16/0808; A61M 16/0833; A61M 16/108; A61M 16/024; A61M 16/107; A61M 16/0066; A61M 16/1085; A61M 16/1005; A61M 16/125; A61M 16/208; A61M 2016/0027; A61M 2016/0039; A61M 2205/3334; A61M 2205/75; A61M 2205/502; A61M 2205/7536; A61M 2205/7545; A61M 2205/3331; C25B 1/04; C25B 9/19; C25B 9/75; C25B 9/77; C25B 15/08; C25B 15/085; C25B 15/087
    See application file for complete search history.

(56)                  References Cited

U.S. PATENT DOCUMENTS

| | | | |
|---|---|---|---|
| 2005/0136299 A1* | 6/2005 | Richey, II | A61M 16/101 |
| | | | 429/444 |
| 2010/0095959 A1 | 4/2010 | Farrell | |
| 2010/0168599 A1* | 7/2010 | Esposito | A61M 16/0858 |
| | | | 600/532 |
| 2010/0186742 A1* | 7/2010 | Sherman | A61M 16/024 |
| | | | 128/204.23 |
| 2011/0147202 A1* | 6/2011 | Haryu | C25B 9/73 |
| | | | 204/257 |
| 2013/0206586 A1* | 8/2013 | Lin | C25B 15/02 |
| | | | 204/230.2 |
| 2014/0048067 A1* | 2/2014 | McGill | C25B 11/02 |
| | | | 204/266 |
| 2014/0378745 A1* | 12/2014 | Lin | A61M 16/122 |
| | | | 600/27 |
| 2015/0101601 A1* | 4/2015 | Lin | C25B 15/08 |
| | | | 128/202.26 |
| 2015/0144482 A1* | 5/2015 | Lin | C25B 9/65 |
| | | | 204/270 |
| 2015/0190604 A1* | 7/2015 | Lin | A61M 16/0833 |
| | | | 128/202.26 |
| 2015/0297513 A1* | 10/2015 | Lin | A61K 9/008 |
| | | | 514/179 |
| 2015/0359979 A1 | 12/2015 | Nagata | |
| 2016/0199603 A1 | 7/2016 | Kawamura | |
| 2016/0263341 A1* | 9/2016 | Lin | C25B 9/17 |
| 2016/0325055 A1* | 11/2016 | Cameron | A24F 40/50 |
| 2016/0331034 A1* | 11/2016 | Cameron | A61M 15/0003 |
| 2017/0106161 A1* | 4/2017 | Lin | A61M 16/0875 |
| 2018/0002822 A1* | 1/2018 | Lin | C25B 13/02 |
| 2018/0028774 A1* | 2/2018 | Lin | A61M 16/12 |
| 2018/0056021 A1* | 3/2018 | Lin | C25B 15/00 |

| | | | |
|---|---|---|---|
| 2019/0062932 A1 | 2/2019 | Lin | |
| 2019/0091436 A1 | 3/2019 | Hsueh | |
| 2019/0126096 A1 | 5/2019 | Squibb | |
| 2019/0192806 A1* | 6/2019 | Bahar | C25B 9/73 |
| 2019/0351177 A1* | 11/2019 | Higuchi | A61M 16/12 |
| 2020/0297963 A1* | 9/2020 | Hsueh | C25B 15/08 |
| 2022/0259745 A1* | 8/2022 | Danyi | C25B 1/02 |

FOREIGN PATENT DOCUMENTS

| | | | | | |
|---|---|---|---|---|---|
| CN | 105163788 A | | 12/2015 | | |
| CN | 106435633 A | | 2/2017 | | |
| CN | 107261273 A | | 10/2017 | | |
| CN | 108411327 A | * | 8/2018 | | C25B 9/70 |
| CN | 208008909 U | | 10/2018 | | |
| CN | 208965047 U | | 6/2019 | | |
| EP | 3447169 A2 | | 2/2019 | | |
| JP | H0819610 A | | 1/1993 | | |
| JP | 2005087257 A | | 4/2005 | | |
| JP | 2007508052 A | | 4/2007 | | |
| JP | 2008200112 A | | 9/2008 | | |
| JP | 2009533199 A | | 9/2009 | | |
| JP | 2010284394 A | | 12/2010 | | |
| JP | 2018525525 A | | 9/2018 | | |
| JP | 2019039069 A | | 3/2019 | | |
| JP | 2019516484 A | | 6/2019 | | |
| WO | 2014024984 A1 | | 2/2014 | | |
| WO | 2014186584 A1 | | 11/2014 | | |
| WO | 2015029838 A1 | | 3/2015 | | |
| WO | 2017020825 A1 | | 2/2017 | | |
| WO | 2017149684 A1 | | 9/2017 | | |

OTHER PUBLICATIONS

First Office Action issued to Japanese Counterpart Application No. 2022-506201 on Jan. 31, 2023 with English Translation.
Invitation to Respond to Written Opinion dated Oct. 11, 2022 for related SG Patent Application No. 11202200900U.
Notice of First Office Action mailed to Corresponding Foreign Patent Application No. 10202400650V dated Apr. 22, 2024.
European Search Report mailed to Corresponding Patent Application No. 20849977.2-1122/4005619 PCT/CN2020097612 on Oct. 20, 2023.
Partial Supplementary European Search Report mailed to Corresponding Patent Application No. 20849977.2-1122/4005619 PCT/CN2020097612 on Jul. 17, 2023.
International Preliminary Report on Patentability dated Feb. 8, 2022 for related International Application No. PCT/CN2020/097612.
International Search Report dated Oct. 10, 2020 for related International Application No. PCT/CN2020/097612.
Office Action mailed to Corresponding Japanese Patent Application No. 2022506201 dated Dec. 24, 2024 with attached English Translation.

\* cited by examiner

BREATHING EQUIPMENT FOR PROVIDING POSITIVE PRESSURE GAS

The present application is based on, and claims priority from, China application number 201910720008.8, filed on 2019 Aug. 6, the disclosure of which is hereby incorporated by reference herein in its entirety.

BACKGROUND OF THE INVENTION

Field of the Invention

The present invention relates to a breathing equipment provided for patients with respiratory disorders, and more particularly to a breathing equipment that generates gas by itself and provides positive pressure gas.

Description of the Prior Art

For long time, people have paid much attention on human life. Many medical technologies have been developed to fight disease and extend human life, but most medical treatments in the past are passive. That is to say, the disease is treated when it occurs, such as surgery, drug administration, chemotherapy and radiotherapy of the cancer, or nursery, rehabilitation, and correction of the chronic disease. However, in recent years, many medical experts have gradually focused research on preventive medical methods, such as health food research, genetic disease screening, and early prevention, to actively prevent future morbidity. In addition, in order to extend human life, many anti-aging and anti-oxidation technologies have been developed and widely used by the public, including smear-care products and antioxidant foods/drugs.

Studies have found that the unstable oxygen (O+), also known as free radicals (harmful free radicals) which is produced by the human body for various reasons such as disease, diet, environment or lifestyle, can be mixed with the inhaled hydrogen to form part of water and then to get excreted so that the number of free radicals in the human body is reduced to regain a healthy alkaline body from an acidic body, to resist oxidation and aging, to eliminate chronic disease, and to achieve beauty care effects. Clinical trials have also shown that some long-term bedridden patients who have lung damage caused by long-term breathing high concentrations of oxygen feel relieved by inhaling hydrogen.

However, patients with obstructive sleep apnea (OSA) who are not bedridden for a long time but need to be treated with positive pressure breathing equipment while sleeping may also have similar problems. Traditional breathing equipment for providing positive pressure gas delivers "continuous positive pressure gas" via a non-invasive breathing mask to obstructive sleep apnea patients who can breathe spontaneously when they are awake. Traditional breathing equipment for providing positive pressure gas raises the pressure of the gas required by the user in the inhalation section to a pressure higher than the atmospheric pressure until the end of the expiration section. When the user inhales, the breathing equipment injects positive pressure gas higher than atmospheric pressure to the user's upper airway, and the user's upper airway dilator muscles will achieve continuous expansion action with the assistance of the positive pressure gas until there is enough muscle tension to open the upper airway to overcome the resistance caused by the lack of muscle tension of the dilator muscles, so that the user can complete the entire inhalation action.

The main cause of obstructive sleep apnea is that the airway is closed due to insufficient muscle tone of the upper airway dilator when the user inhales during sleep. Therefore, the breathing equipment for providing positive pressure gas used by obstructive sleep apnea patients must be matched with a certain gas pressure to achieve the therapeutic effect. In addition to obstructive sleep apnea, Cheyne-Stokes Respiration (CSR), Obesity Hyperventilation (OHS), Chronic Obstructive Pulmonary Disease (COPD) Patients with respiratory disorders will also use breathing equipment for providing positive pressure gas for treatment. However, the continuous positive pressure method also generates positive pressure during exhalation, which sometimes causes discomfort for the user to exhale.

Therefore, there is a need for breathing equipment for providing positive pressure gas that can match the user's breathing rate. During the inhalation period, the breathing equipment can generate positive pressure air to enter the patient's lungs through the airway and cause the lungs to expand. When exhaling, there is no need to generate positive pressure for allowing the end of the tube of the breathing equipment to open to the outside and allowing the gas to discharge by itself.

SUMMARY OF THE INVENTION

In response to the above-mentioned problems, an objective of the present invention is to provide one breathing equipment for providing positive pressure gas. The breathing equipment comprises a gas channel, a hydrogen generating device, a pressurizing device, a mixing device, an atomizing device and an output device. The hydrogen generating device is coupled to the gas channel and is configured to electrolyze water to generate a gas comprising hydrogen. The pressurizing device is coupled to the gas channel and is configured to selectively accelerate an external gas to generate an accelerating gas. The mixing device is coupled to the gas channel and is configured to mix the gas comprising hydrogen and the accelerating gas to generate the positive pressure gas. The atomizing device is coupled to the gas channel and is configured to selectively generate an atomizing gas. The output device is coupled to the gas channel and is configured to selectively output the gas comprising hydrogen, the positive pressure gas, the gas comprising hydrogen with the atomizing gas, or the positive pressure gas with the atomizing gas.

Wherein the breathing equipment further comprises a breathing abnormality detector and a monitoring device. The breathing abnormality detector is coupled to the gas channel and is configured for detecting whether a breathing abnormality occurs on a user who uses the breathing equipment and selectively generates an abnormal signal. The monitoring device is coupled to the breathing abnormality detector, and is configured for activating the pressurizing device to generate the accelerating gas according to the abnormal signal.

Wherein, when the monitoring device activates the pressurizing device, the output device outputs the positive pressure gas, or the positive pressure gas with the atomizing gas. When the monitoring device does not activate the pressurizing device, the output device outputs the gas comprising hydrogen, or the gas comprising hydrogen with the atomizing gas.

Wherein the breathing equipment further comprises an atomizing device switch. When the monitoring device activates the pressurizing device and the atomizing device switch, the output device outputs the positive pressure gas with the atomizing gas. When the monitoring device does not activate the pressurizing device but activates the atomizing device switch, the output device outputs the gas comprising hydrogen with the atomizing gas.

Wherein the pressurizing device further comprises a filter, a fan device and a first flow sensor. The filter is configured to filter out the impurities in the external gas. The fan device is coupled to the filter, and is configured to accelerate the external air after filtering to generate the accelerating gas or a pressuring gas. The first flow sensor is coupled to the fan device, and is configured to detect the flow rate of the accelerating gas and transmit the value of the flow rate to the monitoring device.

Wherein the breathing equipment further comprises a first one-way valve, a first flame arrestor, a second one-way valve and a second flame arrestor. The first one-way valve and the first flame arrestor are configured between the hydrogen generating device and the mixing device. The second flame arrestor is configured between the output device and the mixing device. The second one-way valve is configured between the pressurizing device and the mixing device.

Wherein the breathing equipment further comprises a trigger switch and a monitoring device. The trigger switch is configured for a user to choose whether to activate the pressurizing device and selectively generates a trigger signal. The monitoring device is coupled to the trigger switch and is configured for activating the pressurizing device to generate the accelerating gas according to the trigger signal.

Wherein the breathing equipment further comprises a transmission device being coupled with a monitoring device. The transmission device is configured to receive a breathing adjustment parameter and transmit it to the monitoring device. The monitoring device is configured to receive the breathing adjustment parameter and selectively adjust the flow rate of the accelerating gas according to the breathing adjustment parameter.

Wherein the breathing equipment further comprises a water vapor condensing pipe coupled to the output device. The water vapor condensing pipe is configured to condense the water from a gas outputted by the output device, and the gas is the gas comprising hydrogen, the positive pressure gas, the gas comprising hydrogen with the atomizing gas, or the positive pressure gas with the atomizing gas.

Wherein the hydrogen generating device further comprises a water tank, an electrolysis device, a condense filter and a humidify device. The water tank is configured to accommodate the water. The electrolysis device is configured in the water tank, and is configured to electrolyze the water to generate the gas comprising hydrogen. The condense filter comprises an integrated flow channel and a filtering material configured in the integrated flow channel. The filtering material of the condense filter is configured to filter out an electrolyte from the gas comprising hydrogen, wherein the condense filter receives replenishing water to flush the electrolyte remaining in the filtering material back to the water tank. The humidify device is configured to accommodate the replenishing water for humidifying the gas comprising hydrogen, and provide the replenishing water to the condense filter.

Wherein the integrated flow channel comprises an upper cover and a lower cover. The upper cover combines with the lower cover to form a condensing flow channel, a humidifying flow channel and an output flow channel, and the lower cover is an integrally formed structure. The lower cover has a condensing flow channel inlet and a condensing flow channel outlet connected with the condensing flow channel, a humidifying flow channel inlet and a humidifying flow channel outlet connected with the humidifying flow channel, and an output flow channel inlet and an output flow channel outlet connected with the output flow channel.

Wherein the condensing flow channel inlet communicates with the water tank to receive the gas comprising hydrogen, and the filtering material is configured in the condensing flow channel.

Wherein the humidify device is embedded with the lower cover to communicate with the condensing flow channel outlet and humidifying flow channel inlet. The humidify device is configured to humidify the gas comprising hydrogen and send the gas comprising hydrogen to the humidifying flow channel. The humidify device comprises a humidifying chamber and a communicating chamber. The humidifying chamber is configured to humidify the gas comprising hydrogen, the communicating chamber is configured to communicate the water tank and the condense filter, and the communicating chamber does not communicate with the humidifying chamber.

Wherein the atomizing device is coupled to the output flow channel outlet.

Wherein the hydrogen generating device further comprises an expanded ion-exchange membrane electrolysis device. The expanded ion-exchange membrane electrolysis device comprises an anode plate, a cathode plate, a first bipolar electrode plate, and a first oxygen chamber. The first bipolar electrode plate is configured between the anode plate and the cathode plate. A first ion-exchange membrane plate is accommodated between the anode plate and the first bipolar electrode plate, and a second ion-exchange membrane plate is accommodated between the cathode plate and the first bipolar electrode plate. The first oxygen chamber is adjacent to the anode plate, a first hydrogen chamber is adjacent to the cathode plate, a second oxygen chamber is adjacent to an anode surface of the first bipolar electrode plate, and a second hydrogen chamber is adjacent to a cathode surface of the first bipolar electrode plate. The first oxygen chamber communicates with the second oxygen chamber through an oxygen outlet channel, and the first hydrogen chamber communicates with the second hydrogen chamber through a hydrogen outlet channel.

Wherein the expanded ion-exchange membrane electrolysis device further comprises a second bipolar electrode plate configured between the anode plate and the cathode plate. A third oxygen chamber is adjacent to an anode surface of the second bipolar electrode plate. A third hydrogen chamber is adjacent to a cathode surface of the second bipolar electrode plate. The third oxygen chamber communicates with the first oxygen chamber and the second oxygen chamber through the oxygen outlet channel, and the third hydrogen chamber communicates with the first hydrogen chamber and the second hydrogen chamber through the hydrogen outlet channel.

Wherein the expanded ion-exchange membrane electrolysis device further comprises an oxygen conduit and a hydrogen conduit. The oxygen outlet channel penetrates the cathode plate or the anode plate to connect to the oxygen conduit, and the hydrogen outlet channel penetrates the cathode plate or the anode plate to connect to the hydrogen conduit.

Other objective of the present invention is to provide the breathing equipment for providing a positive pressure gas. The breathing equipment comprises a gas channel, a hydrogen generating device, a pressurizing device, a monitoring device, a mixing device and an atomizing device. The hydrogen generating device is coupled to the gas channel and is configured to electrolyze water to generate a gas comprising hydrogen and oxygen. The pressurizing device is coupled to the gas channel and is configured to selectively accelerate an external gas to generate an accelerating gas. The monitoring device is coupled to the pressurizing device, and is configured to detect a gas signal to control the pressurizing device to generate the accelerating gas. The mixing device is coupled to the gas channel and is configured to mix the gas comprising hydrogen and oxygen with the accelerating gas to generate a positive pressure gas. The atomizing device is coupled to the gas channel and is configured to selectively generate an atomizing gas to be mixed with the positive pressure gas.

Wherein the monitoring device is configured to sense a breathing frequency of a user, and the breathing equipment periodically generates the positive pressure gas based on the breathing frequency.

Wherein the breathing equipment further comprises a first one-way valve, a first flame arrestor, a second one-way valve and a second flame arrestor. The first one-way valve and the first flame arrestor are configured between the hydrogen generating device and the mixing device. The second flame arrestor is configured between the output device and the mixing device. The second one-way valve is configured between the pressurizing device and the mixing device.

Wherein the atomizing device or the pressurizing device has a heating function, to raise the temperature of the atomizing gas or the accelerating gas.

Wherein the hydrogen generating device further comprises a water tank, an electrolysis device, a condense filter and a humidify device. The water tank is configured to accommodate the water. The electrolysis device is configured in the water tank and is configured to electrolyze the water to generate the gas comprising hydrogen and oxygen. The condense filter comprises an integrated flow channel and a filtering material configured in the integrated flow channel. The filtering material of the condense filter is configured to filter out an electrolyte from the gas comprising hydrogen and oxygen. The humidify device is configured to accommodate replenishing water for humidifying the gas comprising hydrogen and oxygen. The condense filter receives the replenishing water from the humidify device to flush the electrolyte filtered by the condense filter back to the water tank.

Wherein the integrated flow channel comprises an upper cover and a lower cover. The upper cover combines with the lower cover to form a condensing flow channel, a humidifying flow channel and an output flow channel, and the lower cover is an integrally formed structure. The lower cover has a condensing flow channel inlet and a condensing flow channel outlet connected with the condensing flow channel, a humidifying flow channel inlet and a humidifying flow channel outlet connected with the humidifying flow channel, and an output flow channel inlet and an output flow channel outlet connected with the output flow channel. The condensing flow channel inlet is connected to the water tank to receive the gas comprising hydrogen and oxygen. The humidify device is fitted with the lower cover to respectively communicate with the condensing flow channel outlet and the humidifying flow channel inlet to humidify the gas comprising hydrogen and oxygen and send the gas comprising hydrogen and oxygen to the humidifying flow channel.

Compared with the prior art, the breathing equipment for providing a positive pressure gas of the present invention can not only help users with obstructive apneas to slow down the occurrence of respiratory cessation during sleep, but also provide self-made gas comprising hydrogen for users to inhale. Therefore, users who use the breathing equipment for a long time can alleviate the oxidative damage that may be caused by positive pressure ventilation. Namely, this oxidative damage is caused by the breathing equipment used by a user who continuously inhales excess gas at a positive pressure. Excessive breathing of oxygen may cause the user's body to expand the alveoli, and the excessive gas that is not needed may run into the gastrointestinal tract, enter the body space and then make the user's body bear the oxidative damage. The breathing equipment of the present invention adds the gas comprising hydrogen to the positive pressure gas to reduce the oxidative damage caused by excessive oxygen.

BRIEF DESCRIPTION OF THE APPENDED DRAWINGS

Some of the embodiments will be described in detail, with reference to the following figures, wherein like designations denote like members, wherein.

The advantages, spirits, and features of the present invention will be explained and discussed with embodiments and figures as follows.

DETAILED DESCRIPTION OF THE INVENTION

In order to make advantages, spirit and character of the present invention more easily, it will be described and discussed in detail by reference attached figure with embodiment. It is worth nothing that theses embodiment only replaced of the invention. But it is implemented in many different forms and is not limited to the embodiments which described in this specification. In contrast, these embodiments are provided to make the public content of the present invention more thorough and comprehensive.

The terminology used in the in the description of the present invention is for the purpose of describing particular embodiments only and does not limit the public embodiments of the present invention. The singular form also includes the plural form unless the context clearly indicates. Unless otherwise defined, all terminology which used in the present specification (included technical and scientific terminology) has the same meanings of the present each public embodiment which ordinary technician can comprehend. The above terminology will be described as the identical meaning of the same field in technology and it will not be explained as ideal meaning or too official meaning, besides it is clearly limited in each embodiments of the present public invention.

In the description of the present specification, the terminologies "in an embodiment", "in another embodiment" means that the specific feature, structure, material or characteristic of the present embodiment is involved in at least one embodiment of the present invention. In the description of the present specification, the schematic representation of the mentioned terminologies does not necessarily refer to the same embodiment. Furthermore, the described specific feature, structure, material or characteristic is involved in any one or more embodiments in a proper way.

In the description of the present invention, unless otherwise specified or limited, the terms "initial connection", "connection", and "setting" should be interpreted in a broad meaning. Such as it is mechanical or electrical connection, it can also be the internal connection of two elements, it is directly connected, and it can also be indirectly connected through an intermediate medium. For those of ordinary technician in the art, the specific meanings of the above terms is understood according to specific circumstances.

Figure 1:
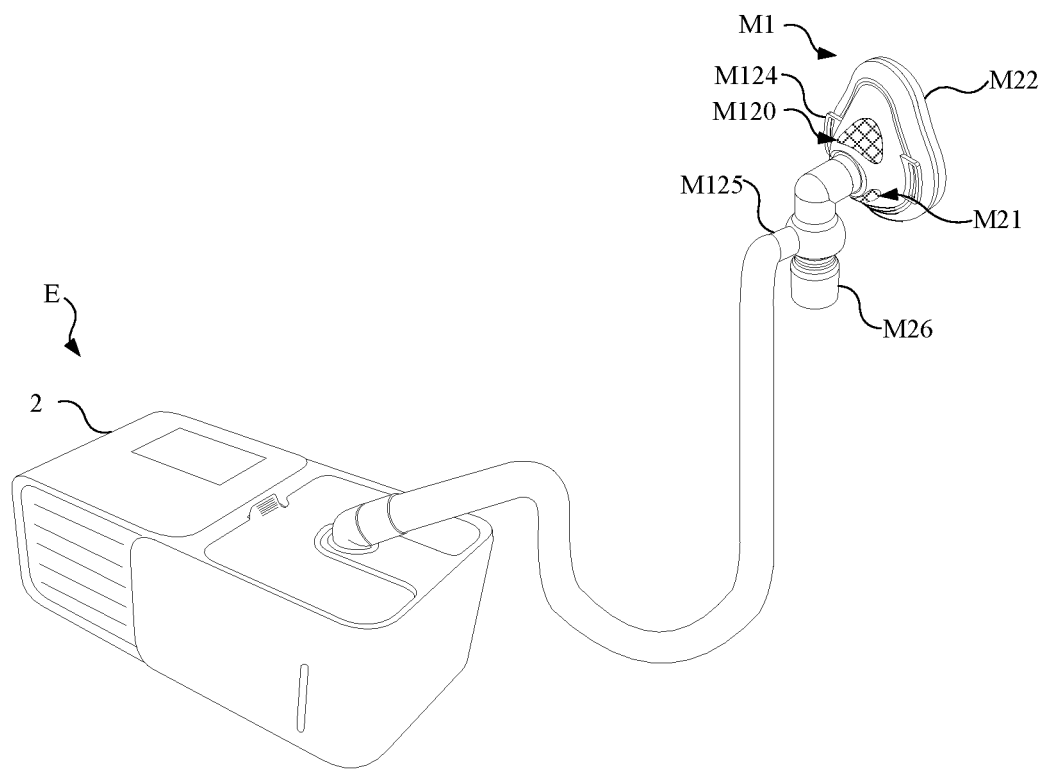
FIG. 1 is a schematic diagram illustrating the appearance of the breathing equipment according to an embodiment of the present invention.
Figure 2:
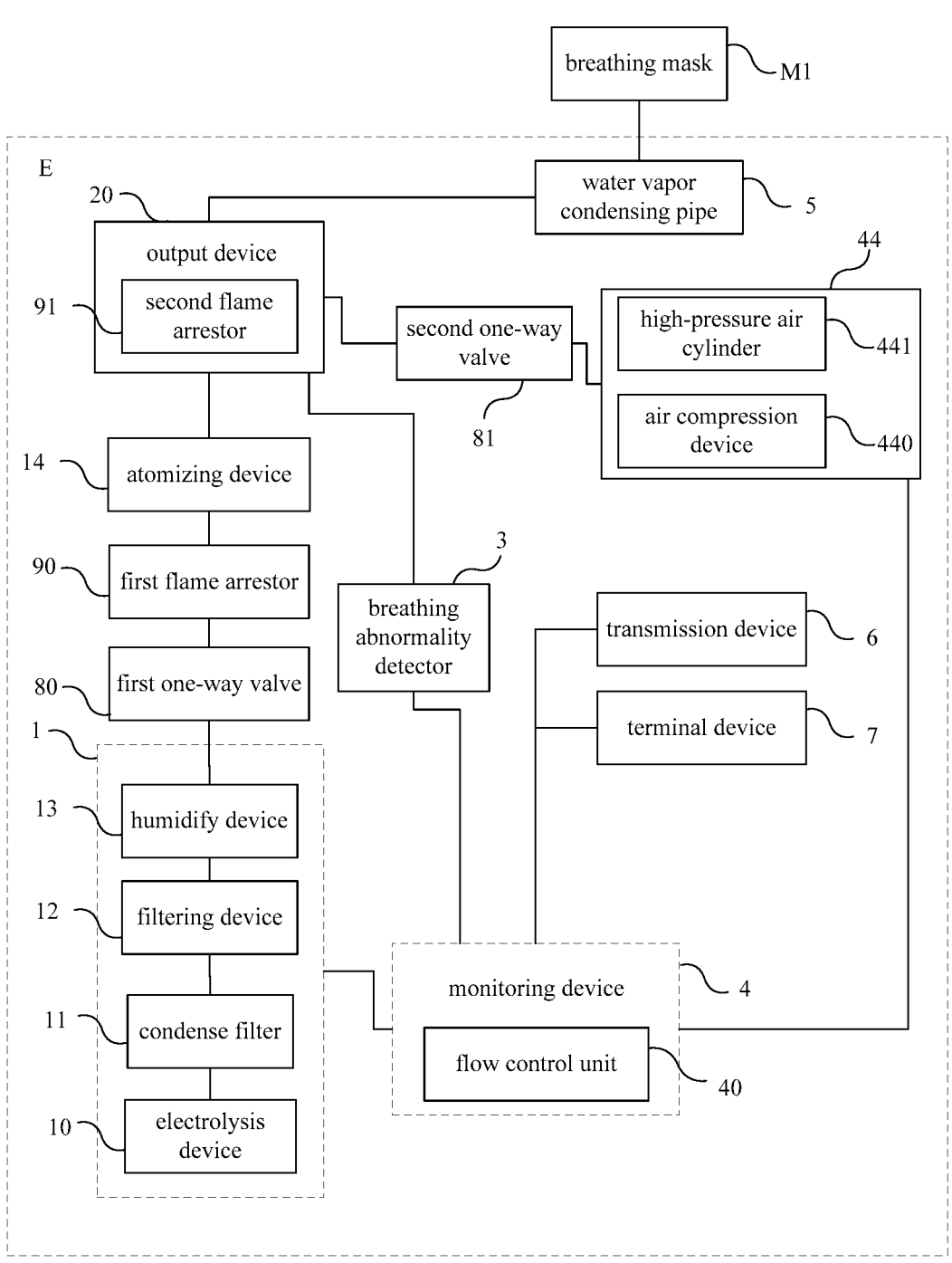
FIG. 2 is a function block diagram illustrating the breathing equipment according to an embodiment of the present invention.

Please refer to FIG. 1 and FIG. 2. FIG. 1 is a schematic diagram illustrating the appearance of the breathing equipment E according to an embodiment of the present invention. FIG. 2 is a function block diagram illustrating the breathing equipment E according to an embodiment of the present invention. As shown in FIG. 1 and FIG. 2, in a specific embodiment, the breathing equipment E for providing positive pressure gas of the present invention includes a hydrogen generating device 1, a case 2, a breathing abnormality detector 3 and a monitoring device 4. The hydrogen generating device 1 is configured to electrolyze water to generate a gas comprising hydrogen. The case 2 comprises an output device 20. The output device 20 is coupled to the hydrogen generating device 1 to receive the gas comprising hydrogen and output it to the external environment. The breathing abnormality detector 3 is coupled to the output device 20 or the hydrogen generating device 1. The breathing abnormality detector 3 is configured for detecting whether a breathing abnormality occurs on a user who uses the breathing equipment E and generating an abnormal signal. The monitoring device 4 is coupled to the breathing abnormality detector 3 for adjusting the pressure of the gas outputted according to the abnormal signal. In practical applications, the output device 20 of the breathing equipment E of the present invention is coupled to a breathing mask M1. The breathing mask M1 is configured for the user to wear to provide the gas comprising hydrogen for the user to inhale. In a specific embodiment, the hydrogen generating device 1, the breathing abnormality detector 3, and the monitoring device 4 may be installed in the case 2.

As shown in FIG. 2, the breathing equipment E further comprises a pressurizing device 44 coupled to the output device 20. In a specific embodiment, the pressurizing device 44 may be a fan device or an air compression device 440 (such as a blower) coupled to the output device 20. The fan device or the air compression device 440 is configured to draw in and compress air from the external environment to generate pressuring gas or accelerating gas. The air compression device 440 provides the pressuring gas to the output device 20 to adjust the pressure of the gas outputted to the external environment. In another specific embodiment, the pressurizing device 44 may be a high-pressure air cylinder 441. The high-pressure air cylinder 441 stores high-pressure air. The monitoring device 4 provides the positive pressure gas in the high-pressure air cylinder 441 to the output device 20 according to the signal, thereby adjusting the pressure of the gas outputted to the external environment. Wherein, at least one of the above-mentioned air compression device 440 and high-pressure air cylinder 441 is selected for use. In another embodiment, the high-pressure air cylinder 441 can also be a high-pressure oxygen cylinder, and is used in conjunction with the air compression device 440 to adjust the content of hydrogen or oxygen of the gas outputted to the external environment. In practical applications, the breathing equipment E further comprises a second one-way valve 81 configured between the pressurizing device 44 and the output device 20. The second one-way valve 81 is configured to block the gas comprising hydrogen from entering the pressurizing device 44.

The breathing equipment E further comprises a first one-way valve 80 and a first flame arrestor 90 configured between the hydrogen generating device 1 and the output device 20. In practical applications, the first one-way valve 80 is set before the gas comprising hydrogen is mixed with an external gas, so as to prevent the positive pressure gas from returning to the hydrogen generating device 1. Therefore, the setting position of the first one-way valve 80 will be adjusted according to the setting position of the monitoring device 4. In the embodiment shown in FIG. 2, the first one-way valve 80 is configured between a humidify device 13 and an atomizing device 14. The breathing equipment E may further comprise the first flame arrestor 90. The first flame arrestor 90 is configured to prevent the fire from moving to the inside of the hydrogen generating device 1 if the flashover problem occurs when the gas comprising hydrogen is mixed with the external gas. Furthermore, a second flame arrestor 91 is configured inside or outside of the output device 20 to avoid flashing movement into the output device 20 when the gas comprising hydrogen and the external gas are outputted.

Figure 3A:
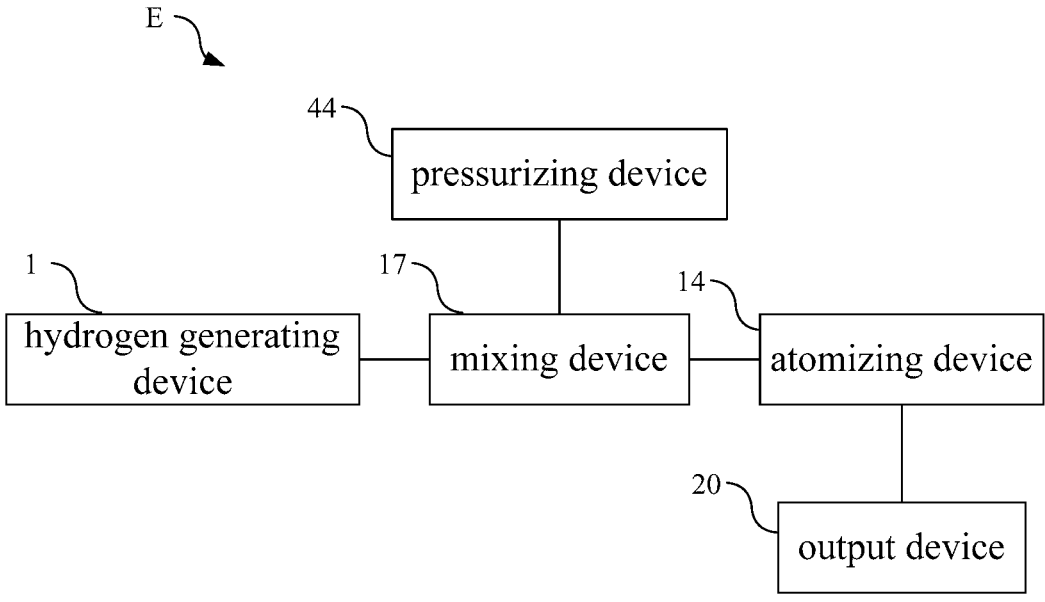
FIG. 3A is a function block diagram illustrating the breathing equipment according to another embodiment of the present invention.

Please refer to FIG. 3A. FIG. 3A is a function block diagram illustrating the breathing equipment E according to another embodiment of the present invention. In the specific embodiment of FIG. 3A, the breathing equipment E comprises a gas channel, the hydrogen generating device 1, the pressurizing device 44, a mixing device 17, the atomizing device 14 and the output device 20. The hydrogen generating device 1 is coupled to the gas channel and is configured to electrolyze water to generate the gas comprising hydrogen. The pressurizing device 44 is coupled to the gas channel and is configured to selectively accelerate the external gas to generate the accelerating gas or the positive pressure gas. The mixing device 14 is coupled to the gas channel and is configured to mix the gas comprising hydrogen and the accelerating gas to generate the positive pressure gas. The atomizing device 14 is coupled to the gas channel and is configured to selectively generate an atomizing gas. The output device 20 is coupled to the gas channel and is configured to selectively output different combinations of the gas comprising hydrogen, the positive pressure gas, the gas comprising hydrogen with the atomizing gas, or the positive pressure gas with the atomizing gas.

Figure 3B:
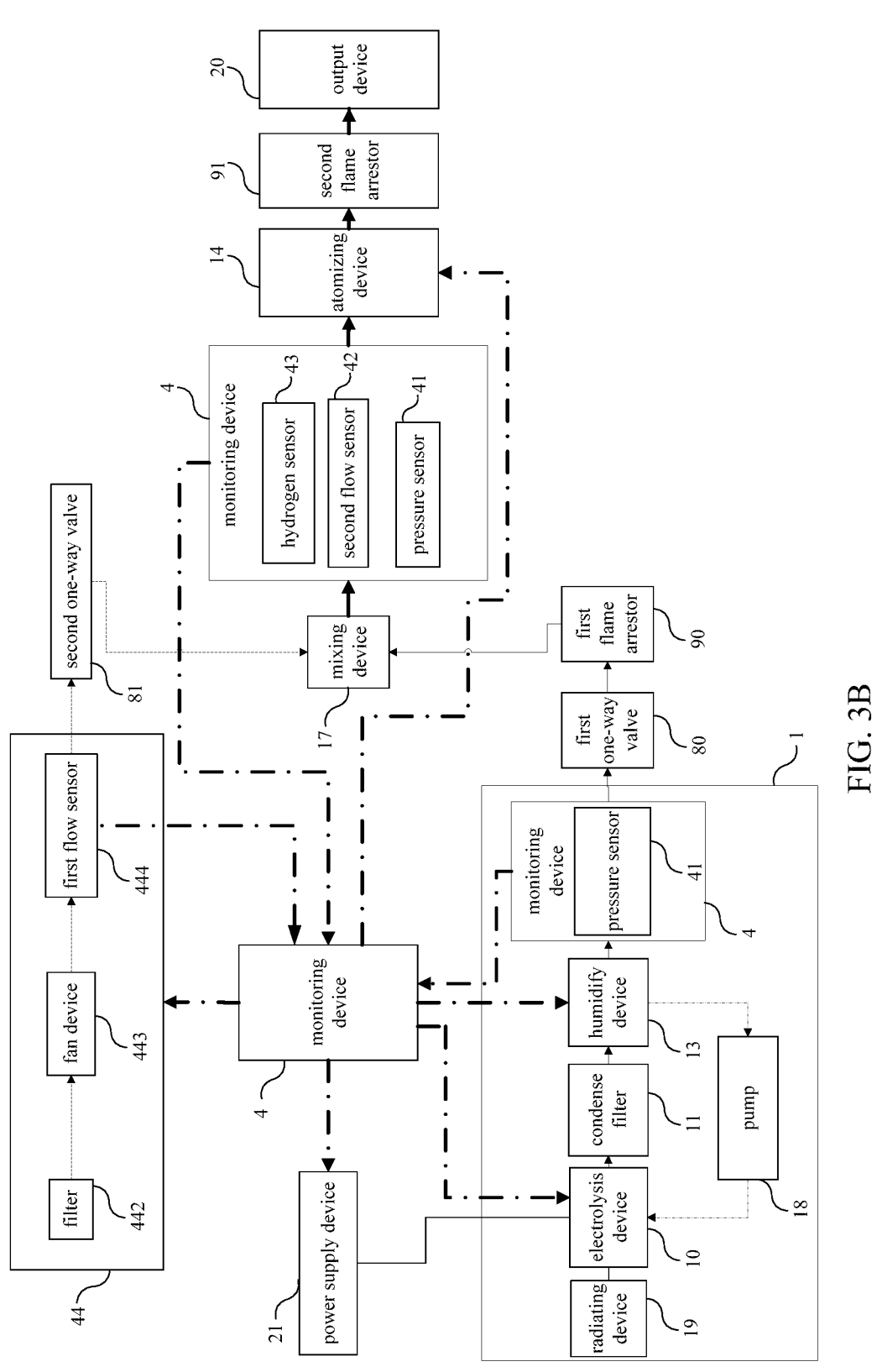
FIG. 3B is a function block diagram illustrating the breathing equipment according to more another embodiment of the present invention.

Please refer to FIG. 3B. FIG. 3B is a function block diagram illustrating the breathing equipment E according to more another embodiment of the present invention. In the specific embodiment of FIG. 3B, the breathing equipment E comprises an electrolysis device 10, a condense filter 11, the humidify device 13, a radiating device 19, a pump 18, the monitoring device 4 (FIG. 3B may include several parts), a power supply device 21, the pressurizing device 44 (comprising a filter 442, air compression device or the fan device 443), the mixing device 17, the atomizing device 14 and the output device 20. The monitoring device 4 can comprise a pressure sensor 41, a second flow sensor 42 and a hydrogen sensor 43. The pressure sensor 41 is configured to sense the pressure value of the gas current outputted. The second flow sensor 42 is configured to sense the flow of the gas current outputted. The hydrogen sensor 43 is configured to sense the concentration of hydrogen from the gas comprising hydrogen current outputted. In one embodiment, the monitoring device 4 can sense the user's breathing rate, and activate the pressurizing device 44 to generate air with positive pressure during the inhalation period. When exhaling, the pressurizing device 44 is closed or reduced the pressure of the gas generated by the pressurizing device 44, so that the user can easily exhale the gas by himself/herself.

The power supply device 21 is coupled to the monitoring device 4 and the electrolysis device 10 to provide power required for operation. The radiating device 19 is coupled to the electrolysis device 10, and is configured to assist the electrolysis device 10 to dissipate heat, so as to avoid overheating that affects the electrolysis efficiency or causes thermal damage to the device. The electrolysis device 10 is coupled to the condense filter 11, the condense filter 11 is coupled to the humidify device 13, the humidify device 13 is coupled to the pressure sensor 41, the pressure sensor 41 is coupled to the first one-way valve 80, the first one-way valve 80 is coupled to the first flame arrestor 90, and the first flame arrestor 90 is coupled to the mixing device 17. The pump 18 is coupled to the humidify device 13 and the electrolysis device 10 to deliver the water from the humidify device 13 to the electrolysis device 10 for the electrolysis device 10 to use as the water to be electrolyzed.

The pressurizing device 44 further comprises the filter 442, the fan device 443, and a first flow sensor 444. The filter 442 filters out the impurities in the external gas. The fan device 443 is coupled to the filter 442. The fan device 443 accelerates the external gas filtered to generate the accelerating gas or the pressuring gas. The first flow sensor 444 is coupled to the fan device 443. The first flow sensor 444 detects the flow rate of the accelerating gas and transmits the value of the flow rate to the monitoring device 4.

The thin solid arrow in FIG. 3B is the flow direction of the gas comprising hydrogen. As shown in FIG. 3B, the gas comprising hydrogen flows from the electrolysis device 10 through the condense filter 11, the humidify device 13, the pressure sensor 41, the first one-way valve 80, the first flame arrestor 90 to the mixing device 17. The thin dashed arrow in FIG. 3B is the flow direction of the accelerating gas or the pressuring gas. As shown in FIG. 3B, the air is filtered from the filter 442, and is generated to the accelerating gas or the pressuring gas by the air compression device or the fan device 443. Then, it flows through the first flow sensor 444 and the second one-way valve 81 to the mixing device 17 to mix with the gas comprising hydrogen. The thick solid arrow in FIG. 3B (for example, from the mixing device 17 to the output device 20) is the flow direction of the positive pressure gas.

The breathing equipment E further comprises the breathing abnormality detector 3 (not shown in FIG. 3B) and the monitoring device 4. The breathing abnormality detector 3 is coupled to the gas channel (for example, the thick solid arrow part in FIG. 3B or other gas flowing parts), and is configured to detect whether a user coupled for detecting whether a breathing abnormality occurs on a user who uses the breathing equipment E and selectively generating an abnormal signal. The monitoring device 4 is coupled to the breathing abnormality detector 3. The monitoring device 4 is configured for activating the pressurizing device 44 to generate the accelerating gas or the pressuring gas according to the abnormal signal. At this time, the monitoring device 4 can generate the positive pressure gas from time to time according to the abnormal signal.

When the monitoring device 4 activates the pressurizing device 44, the output device 20 outputs the positive pressure gas, or the positive pressure gas with the atomizing gas. When the monitoring device 4 does not activate the pressurizing device 44, the output device 20 outputs the gas comprising hydrogen, or the gas comprising hydrogen with the atomizing gas.

The breathing equipment E further comprises an atomizing device switch (not shown in FIG. 3B). When the monitoring device 4 activates the pressurizing device 44 and the atomizing device switch, the output device 20 outputs the positive pressure gas with the atomizing gas. When the monitoring device 4 does not activate the pressurizing device 44 but activates the atomizing device switch, the output device 20 outputs the gas comprising hydrogen with the atomizing gas.

The breathing equipment E further comprises a trigger switch (not shown in FIG. 3B). The trigger switch is configured for a user to choose whether to activate the pressurizing device 44 and selectively generate a trigger signal. The monitoring device 4 is coupled to the trigger switch and is configured for activating the pressurizing device 44 to generate the accelerating gas according to the trigger signal. At this time, the user can choose to generate continuous positive pressure gas.

Please refer to FIG. 3A. The breathing equipment E may additionally comprise a transmission device 6 which is coupled with the monitoring device 4. The transmission device 6 is configured to receive a breathing adjustment parameter and transmit it to the monitoring device 4. The monitoring device 4 is configured to receive the breathing adjustment parameter and selectively adjust the flow rate of the accelerating gas according to the breathing adjustment parameter. At this time, the user can select the period, frequency, pressure and other parameters of the positive pressure gas generated. The breathing equipment E further comprises a water vapor condensing pipe 5 coupled to the output device 20. The water vapor condensing pipe 5 is configured to condense the water from a gas outputted by the output device 20, and the gas can be the gas comprising hydrogen, the positive pressure gas, the gas comprising hydrogen with the atomizing gas, or the positive pressure gas with the atomizing gas. Wherein, in another specific embodiment, the hydrogen generating device 1 is configured to generate gas comprising hydrogen and oxygen.

As shown in FIG. 3B, the mixing device 17 is coupled to the hydrogen sensor 43, the second flow sensor 42 and the pressure sensor 41 of the monitoring device 4. The monitoring device 4 is coupled to the atomizing device 14, the atomizing device 14 is coupled to the second flame arrestor 91, and the second flame arrestor 91 is coupled to the output device 20. As indicated by the thick arrow in FIG. 3B, the gas comprising hydrogen is mixed with the pressuring gas in the mixing device 17. The gas comprising hydrogen mixed flows from the mixing device 17 through the hydrogen sensor 43, the second flow sensor 42, the pressure sensor 41, the atomizing device 14 and the second flame arrestor 91 to the output device 20. Of course, the hydrogen sensor 43, the second flow sensor 42, and the pressure sensor 41 can exist at the same time, or any combination of the three, depending on which detection function is required.

As shown in FIG. 3B, the monitoring device 4 is coupled to the power supply device 21, the electrolysis device 10, the humidify device 13, the atomizing device 14 and the pressurizing device 44. The monitoring device 4 can receive the gas pressure value, the flow value and hydrogen concentration sensed by the pressure sensor 41, the first flow sensor 444, the second flow sensor 42, and the hydrogen sensor 43 to adjust the pressure, flow and hydrogen concentration in real time. These gas pressure values, flow values or hydrogen concentration can all be called as "gas signals". In detail, a dot-chain line in FIG. 3B is the transmission direction of signals and commands. After the first flow sensor 444 coupled to the fan device 443 transmits the current flow rate of the positive pressure gas to the monitoring device 4, the monitoring device 4 can provide acceleration operation information or deceleration operation information according to the current positive pressure gas flow rate to the monitoring device 4 for adjusting the pressure value of the positive pressure gas. When the humidify device 13 coupled to the pressure sensor 41 transmits the current pressure value of the gas comprising hydrogen to the monitoring device 4, the monitoring device 4 can provide the signal of increasing the amount of hydrogen production or the signal of decreasing the amount of hydrogen production to at least one of the power supply device 21 and the electrolysis device 10 according to the current pressure value of the gas comprising hydrogen. In other words, the monitoring device 4 is configured to detect a gas signal to control the pressurizing device 44 to generate the accelerating gas.

The power supply device 21 can increase or decrease the voltage provided to the electrolysis device 10 according to the increasing hydrogen production signal or the decreasing hydrogen production signal, so as to adjust the hydrogen production of the electrolysis device 10. The electrolysis device 10 can increase or decrease the electrolysis rate according to the increasing hydrogen production signal or the decreasing hydrogen production signal, so as to adjust the hydrogen production. After the hydrogen sensor 43, the second flow sensor 42, and the pressure sensor 41 coupled to the mixing device 17 transmit the current hydrogen concentration, flow and pressure value of the positive pressure gas to the monitoring device 4, the monitoring device 4 can provide at least one of the acceleration operation signal or the deceleration operation signal to the pressurizing device 44, the increasing hydrogen production signal or the decreasing hydrogen production signal to the power supply device 21, and the increasing hydrogen production signal or the decreasing hydrogen production signal to the electrolysis device 10 according to the current hydrogen concentration, flow rate and pressure value of the positive pressure gas for adjusting the hydrogen concentration, flow rate and pressure value of the positive pressure gas.

Figure 4:
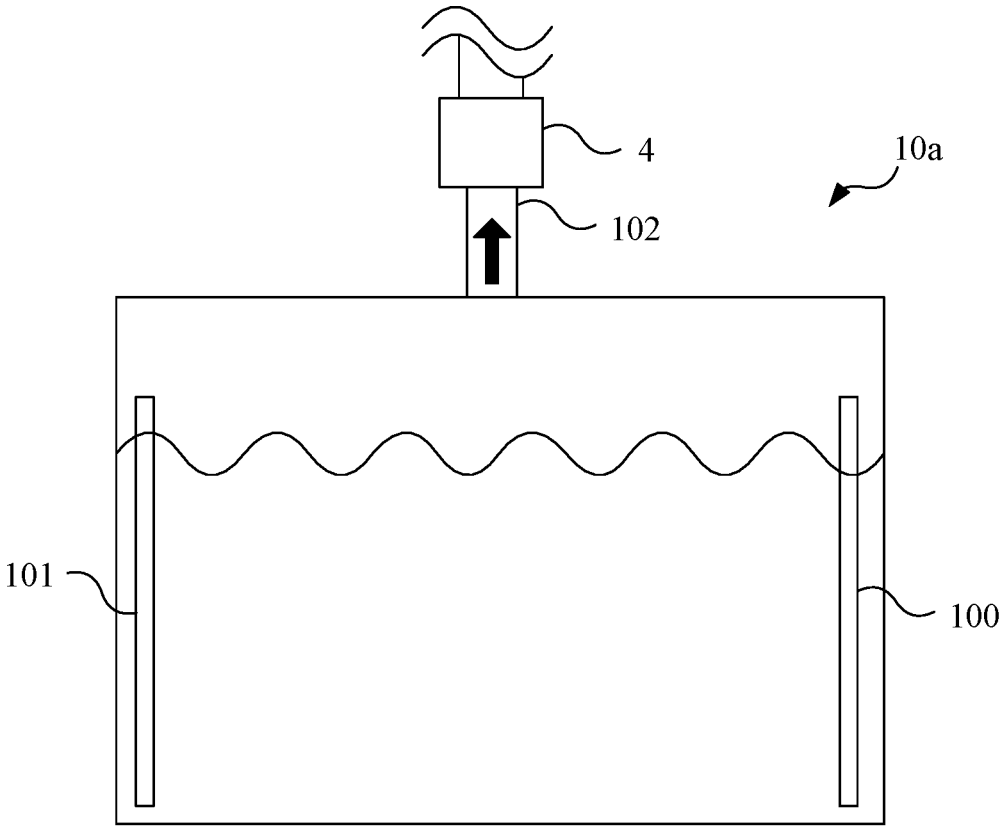
FIG. 4 is a schematic structural diagram illustrating the general electrolysis device of the breathing equipment according to an embodiment of the present invention.

Please refer to FIG. 2 and FIG. 4. FIG. 4 is a schematic structural diagram illustrating the general electrolysis device 10a of the breathing equipment E according to an embodiment of the present invention. In practice, the hydrogen generating device 1 of the breathing equipment E of the present invention comprises the electrolysis device, and the electrolysis device can be divided into a general electrolysis device 10a or an ion-exchange membrane electrolysis device 10b. In a specific embodiment, the electrolysis device is the general electrolysis device 10a having a cathode 100 and an anode 101. When the general electrolysis device 10a is electrolyzing water, the cathode 100 generates hydrogen, and the anode 101 generates oxygen, and then the two are mixed into the gas comprising hydrogen. The general electrolysis device 10a comprises a gas output channel 102 coupled to the output device 20. The gas comprising hydrogen is supplied to the output device 20 through the gas output channel 102 of the general electrolysis device 10a. The monitoring device 4 further comprises a flow control unit 40 coupled to the gas output channel 102, and by adjusting the gas flow input to the output device 20 to adjust the pressure of the gas outputted to the external environment. Wherein, the monitoring device 4 is configured to further mix the gas comprising hydrogen with the external gas to form a gas composition ratio suitable for human inhalation. In practical applications, the breathing mask M1 can be coupled to the output device 20.

Figure 5:
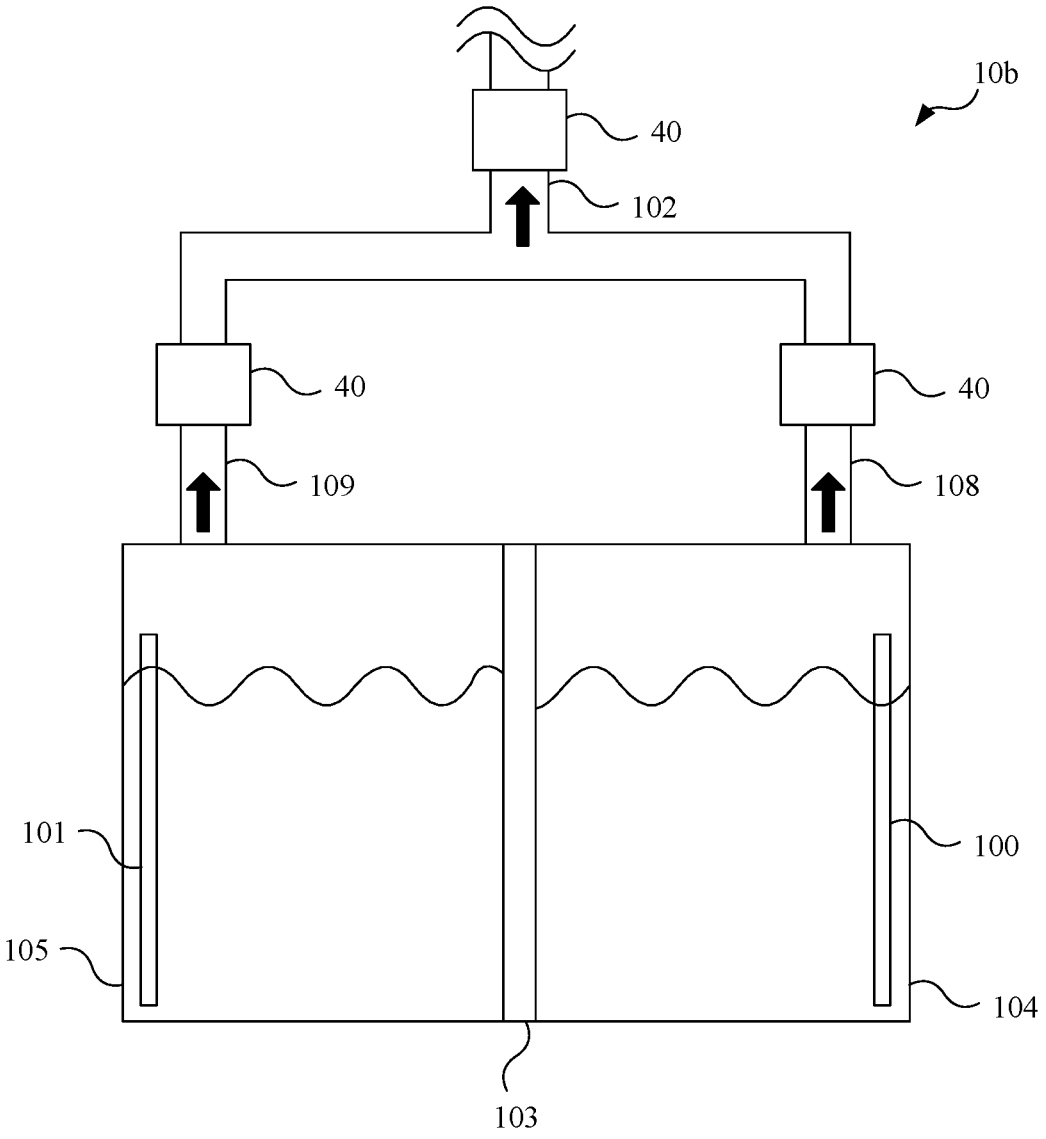
FIG. 5 is a schematic structural diagram illustrating the ion-exchange membrane electrolysis device of the breathing equipment according to an embodiment of the present invention.

Please refer to FIG. 5. FIG. 5 is a schematic structural diagram illustrating the ion-exchange membrane electrolysis device 10b of the breathing equipment E according to an embodiment of the present invention. In a specific embodiment, as shown in FIG. 5, the electrolysis device in the hydrogen generating device 1 is the ion-exchange membrane electrolysis device 10b, which comprises an ion-exchange membrane 103, a cathode chamber 104 and an anode chamber 105. A cathode 100 is configured in the cathode chamber 104, and the anode 101 is configured in the anode chamber 105. The ion-exchange membrane 103 is configured between the cathode chamber 104 and the anode chamber 105. When the ion-exchange membrane electrolysis device 10b electrolyzes water, the anode 101 generates oxygen in the anode chamber 105, and the cathode 100 generates hydrogen in the cathode chamber 104.

Figure 6A:
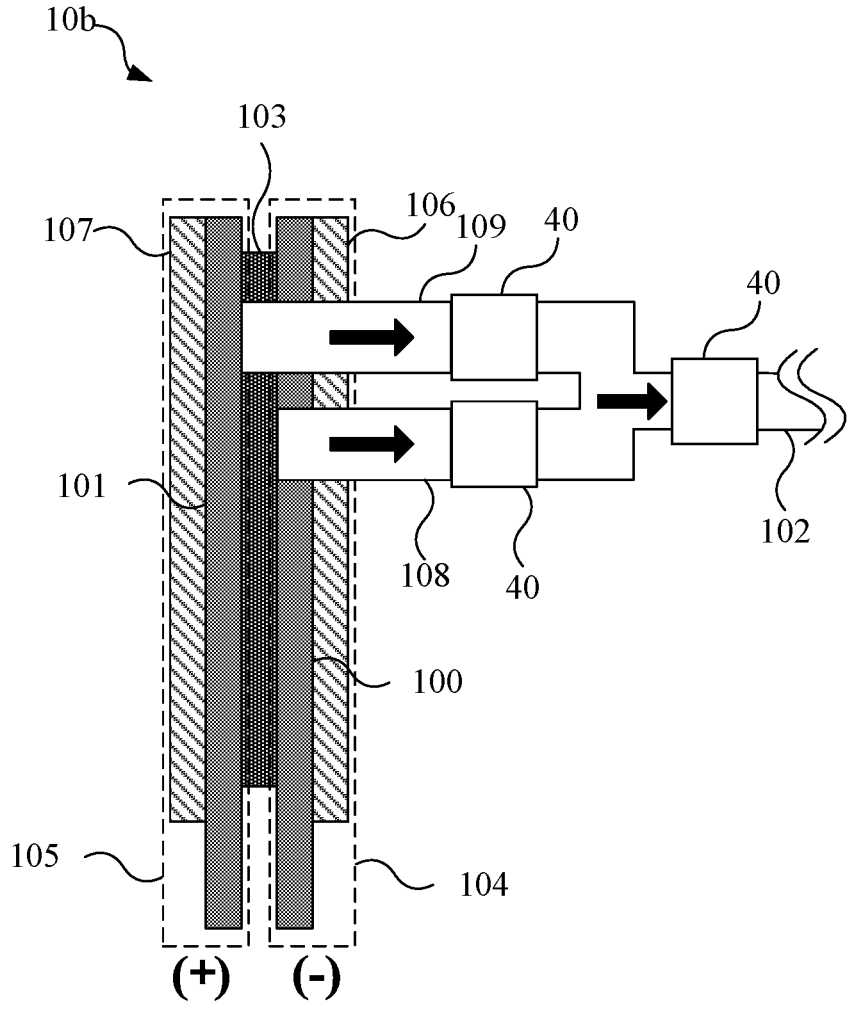
FIG. 6A is a schematic structural diagram illustrating the ion-exchange membrane electrolysis device of the breathing equipment according to another embodiment of the present invention.
Figure 6B:
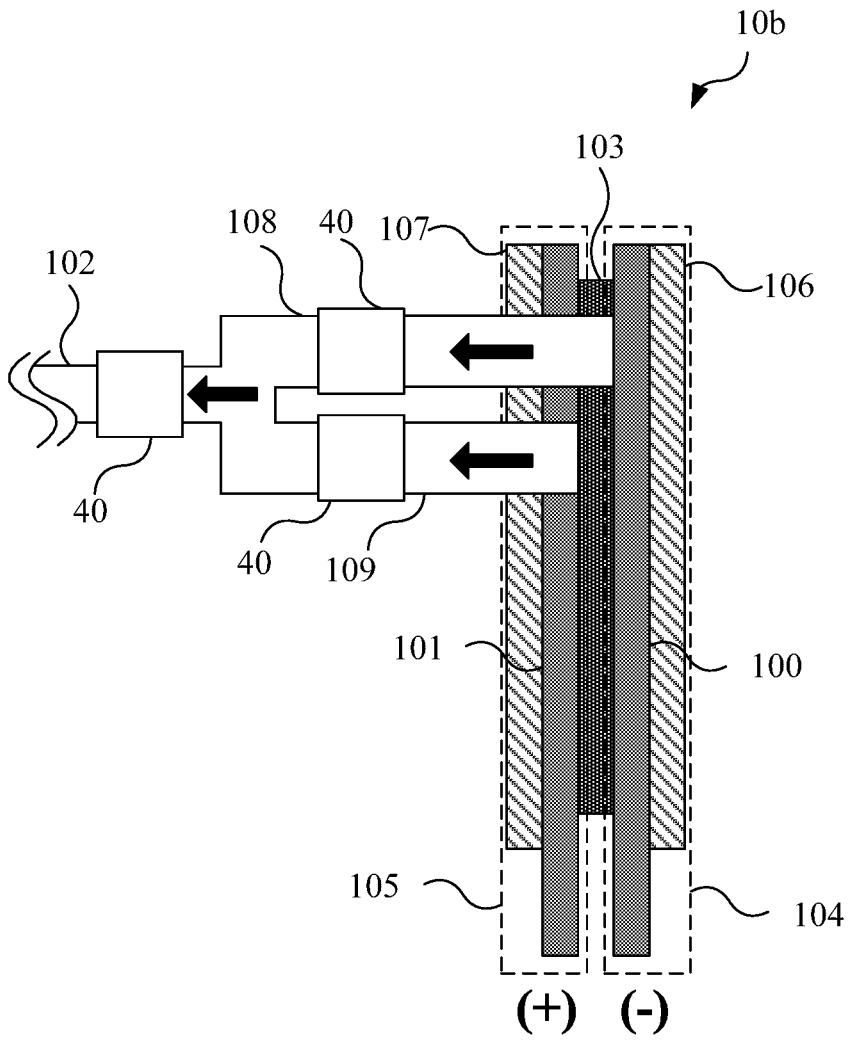
FIG. 6B is a schematic structural diagram illustrating the ion-exchange membrane electrolysis device of the breathing equipment according to another embodiment of the present invention.

Please refer to FIG. 6A and FIG. 6B. FIG. 6A is a schematic structural diagram illustrating the ion-exchange membrane electrolysis device 10b of the breathing equipment E according to another embodiment of the present invention. FIG. 6B is a schematic structural diagram illustrating the ion-exchange membrane electrolysis device 10*b* of the breathing equipment E according to another embodiment of the present invention. This paragraph will briefly describe the main features of the present invention in conjunction with FIG. 6A and FIG. 6B. In the specific embodiment of FIG. 6A and FIG. 6B, the electrolysis device is the ion-exchange membrane electrolysis device 10*b*. The ion-exchange membrane electrolysis device 10*b* comprises the cathode 100, the anode 101, the ion-exchange membrane 103, a first side 106 and a second side 107. The ion-exchange membrane 103 is configured between the first side 106 and the second side 107, the cathode 100 is configured between the ion-exchange membrane 103 and the first side 106, and the anode 101 is configured between the ion-exchange membrane 103 and the second side 107. The area where the first side 106 and the cathode 100 are located is called as the cathode chamber 104, and the area where the second side 107 and the anode 101 are located is called as the anode chamber 105. In order to more clearly express the corresponding positions of the cathode chamber 104 and the anode chamber 105, their positions are indicated by dotted lines in FIG. 6A and FIG. 6B. When the ion-exchange membrane electrolysis device 10*b* electrolyzes water, the anode 101 generates oxygen in the anode chamber 105, and the cathode 100 generates hydrogen in the cathode chamber 104. The ion-exchange membrane electrolysis device 10*b* further comprises a hydrogen channel 108 that communicates with the cathode chamber 104 and the output device 20. To further illustrate, the specific embodiment shown in FIG. 5 is that the hydrogen channel 108 directly communicates with the cathode chamber 104 and the output device 20. As shown in the specific embodiment shown in FIG. 6A, the hydrogen channel 108 extends from between the ion-exchange membrane 103 and the first side 106 to the second side 107 and penetrates the second side 107 to communicate with the output device. In the specific embodiment shown in FIG. 6B, the hydrogen channel 108 extends from between the ion-exchange membrane 103 and the first side 106 to the first side 106 and penetrates the first side 106 to communicate with the output device. In a specific embodiment, the ion-exchange membrane electrolysis device 10*b* further comprises an oxygen channel 109 communicating with the anode chamber 105 and the output device 20. To further illustrate, the specific embodiment shown in FIG. 5 is that the oxygen channel 109 directly communicates with the anode chamber 105 and the output device 20. As shown in the specific embodiment shown in FIG. 6A, the oxygen channel 109 extends from between the ion-exchange membrane 103 and the second side 107 to the second side 107 and penetrates the second side 107 to communicate with the output device 20. As shown in the specific embodiment shown in FIG. 6B, the oxygen channel 109 extends from between the ion-exchange membrane 103 and the second side 107 to the first side 106 and penetrates the first side 106 to communicate with the output device 20. The hydrogen channel 108 and the oxygen channel 109 intersect and communicate to form the gas output channel 102, which further mixes hydrogen and oxygen into the gas comprising hydrogen in a desired ratio. In the above specific embodiment, the hydrogen channel 108, the oxygen channel 109 and the gas outlet channel 102 are respectively connected to the flow control unit 40. The flow control unit 40 controls the mixing ratio of hydrogen and oxygen in the gas comprising hydrogen and the flow rate of the gas comprising hydrogen to the output device 20 according to the signal.

Figure 7:
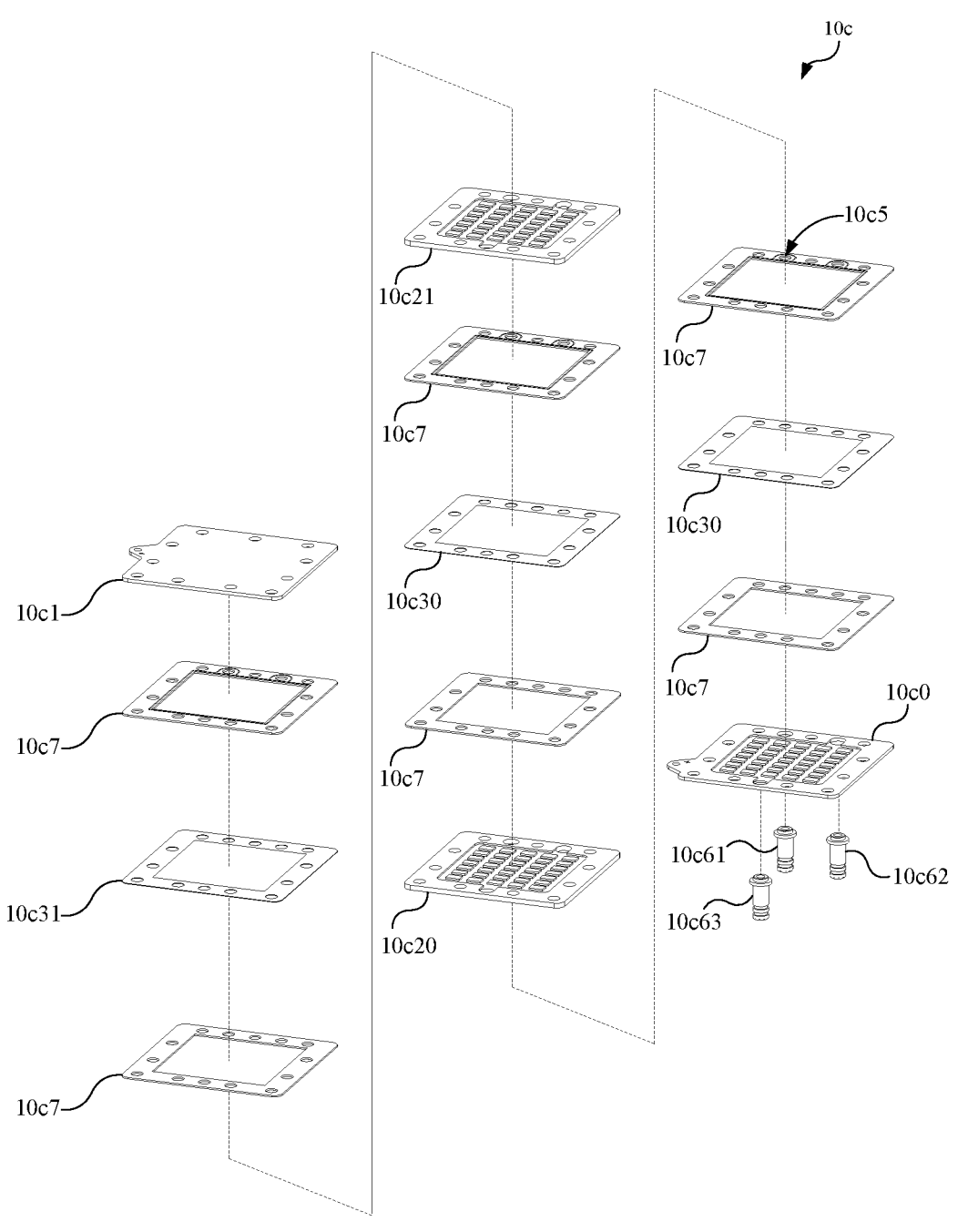
FIG. 7 is a schematic structural diagram illustrating the expanded ion-exchange membrane electrolysis device of the breathing equipment according to an embodiment of the present invention.
Figure 8:
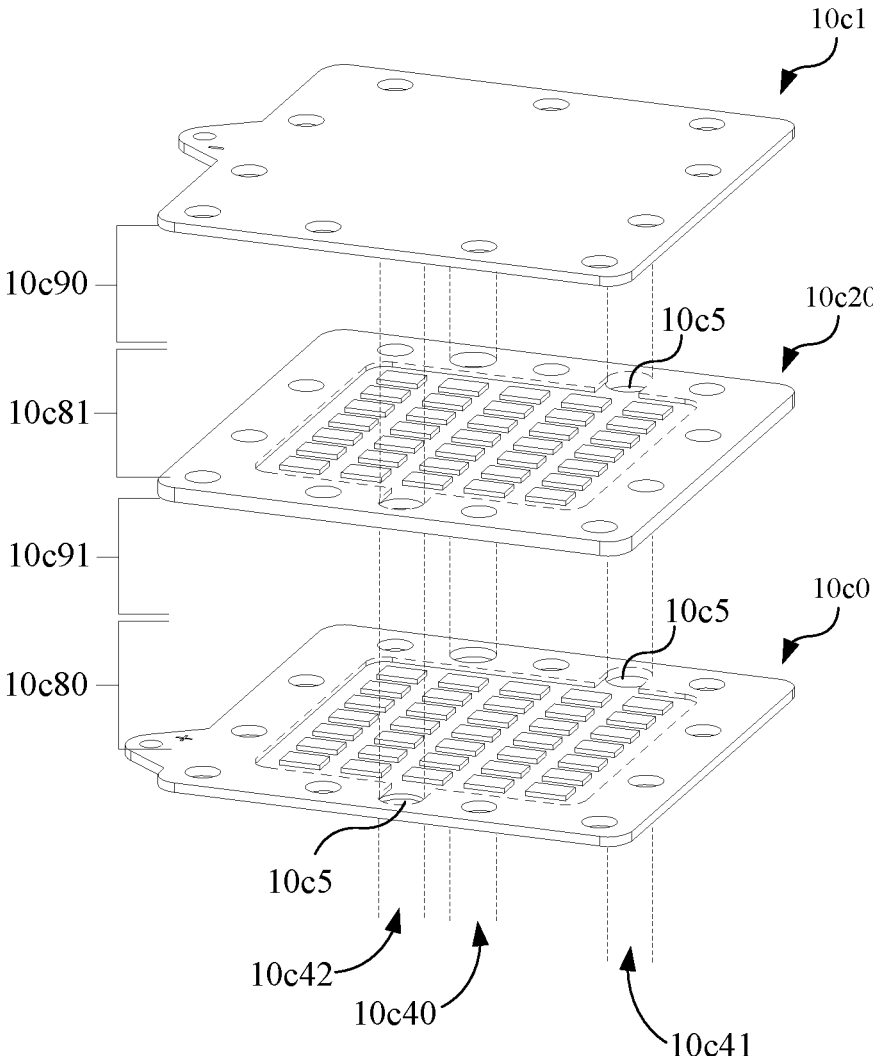
FIG. 8 is a schematic diagram illustrating the hydrogen outlet channel, the oxygen outlet channel and the water inlet channel of the expanded ion-exchange membrane electrolysis device of the breathing equipment according to an embodiment of the present invention.

Please refer to FIG. 7 and FIG. 8. FIG. 7 is a schematic structural diagram illustrating the expanded ion-exchange membrane electrolysis device 10*c* of the breathing equipment E according to an embodiment of the present invention. FIG. 8 is a schematic diagram illustrating the hydrogen outlet channel 10*c*40, the oxygen outlet channel 10*c*41 and the water inlet channel 10*c*42 of the expanded ion-exchange membrane electrolysis device 10*c* of the breathing equipment E according to an embodiment of the present invention. In addition to the above-mentioned electrolysis device, an expanded ion-exchange membrane electrolysis device 10*c* may also be included. As shown in FIG. 7, the expanded ion-exchange membrane electrolysis device 10*c* comprises an anode plate 10*c*0, a cathode plate 10*c*1, and a first bipolar electrode plate 10*c*20. The first bipolar electrode plate 10*c*20 is configured between the anode plate 10*c*0 and the cathode plate 10*c*1. A first ion-exchange membrane plate 10*c*30 is accommodated between the anode plate 10*c*0 and the first bipolar electrode plate 10*c*20, and a second ion-exchange membrane plate 10*c*31 is accommodated between the cathode plate 10*c*1 and the first bipolar electrode plate 10*c*20. As shown in FIG. 8, a first oxygen chamber 10*c*80 is adjacent to the anode plate 10*c*0, a first hydrogen chamber 10*c*90 is adjacent to the cathode plate 10*c*1, a second oxygen chamber 10*c*81 is adjacent to an anode surface of the first bipolar electrode plate 10*c*20, and a second hydrogen chamber 10*c*91 is adjacent to a cathode surface of the first bipolar electrode plate 10*c*20. Wherein, the first oxygen chamber 10*c*90 communicates with the second oxygen chamber 10*c*81 through an oxygen outlet channel 10*c*41, and the first hydrogen chamber 10*c*90 communicates with the second hydrogen chamber 10*c*91 through a hydrogen outlet channel 10*c*40.

In practical applications, the expanded ion-exchange membrane electrolysis device 10*c* can increase the bipolar electrode plate and the ion-exchange membrane plate between the anode plate 10*c*0 and the cathode plate 10*c*1 to expand the electrolysis device, thereby improving the efficiency of electrolysis and the efficiency of gas production. In a specific embodiment, the second bipolar electrode plate 10*c*21 is configured between the anode plate 10*c*0 and the cathode plate 10*c*1. The third oxygen chamber (not shown in the figure) is adjacent to the anode surface of the second bipolar electrode plate 10*c*21, and the third hydrogen chamber (not shown in the figure) is adjacent to the cathode surface of the second bipolar electrode plate 10*c*21. The third oxygen chamber communicates with the first oxygen chamber 10*c*80 and the second oxygen chamber 10*c*81 through the oxygen outlet channel 10*c*41, and the third hydrogen chamber communicates with the first hydrogen chamber 10*c*90 and the second hydrogen chamber 10*c*91 through the hydrogen outlet channel 171. Furthermore, the third oxygen chamber is not connected to the first hydrogen chamber 10*c*90, the second hydrogen chamber 10*c*91, and the third hydrogen chamber, and the third hydrogen chamber is not connected to the first oxygen chamber 10*c*80, the second oxygen chamber 10*c*81, and the third oxygen chamber.

In a further specific embodiment, the expanded ion-exchange membrane electrolysis device further comprises an oxygen conduit 10*c*62 and a hydrogen conduit 10*c*61. The oxygen outlet channel 10*c*41 penetrates the cathode plate 10*c*1 or the anode plate 10*c*0 and is connected to the oxygen conduit 10*c*62. The hydrogen outlet channel 10*c*40 penetrates the cathode plate 10*c*1 or the anode plate 10*c*0 and is connected to the hydrogen conduit 10*c*61. In practical applications, the oxygen conduit 10*c*62 can be connected to the oxygen channel 109, and the hydrogen conduit 10*c*61 can be connected to the hydrogen channel 108, and the hydrogen channel 108 can be connected to the gas output channel 102 to output the gas comprising hydrogen to the output device 20. In another specific embodiment, the hydrogen channel 108 and the oxygen channel 109 may be connected to the gas output channel 102 to mix a specific proportion of the gas comprising hydrogen. The hydrogen channel 108, the oxygen channel 109 and the gas output channel 102 may be coupled to the flow control unit 40. The flow control unit 40 controls the flow of the gas comprising hydrogen to the output device 20 according to the signal.

In order to reduce the possibility of water and air leakage in the expanded ion-exchange membrane electrolysis device 10*c* formed after being stacked on each other, and to allow the hydrogen outlet channel 10*c*40, the oxygen outlet channel 1*c*41, the water inlet channel 1*c*42, and each oxygen chamber and hydrogen chamber to maintain independent spaces, the expanded ion-exchange membrane electrolysis device 10*c* further comprises a plurality of silicone gaskets 10*c*7. Each silicone gasket 10*c*7 is respectively configured between each ion-exchange membrane plate and the corresponding the cathode plate 10*c*1, the anode plate 10*c*0 or the bipolar electrode plates.

Compared with the general electrolysis device 10*a* and the ion-exchange membrane electrolysis device 10*b*, the expanded ion-exchange membrane electrolysis device 10*c* described above is stacked more closely. Therefore, under the same electrolysis efficiency, the expanded ion-exchange membrane electrolysis device 10*c* requires a smaller volume than the other two electrolysis devices, thereby miniaturizing the breathing equipment E.

Figure 9:
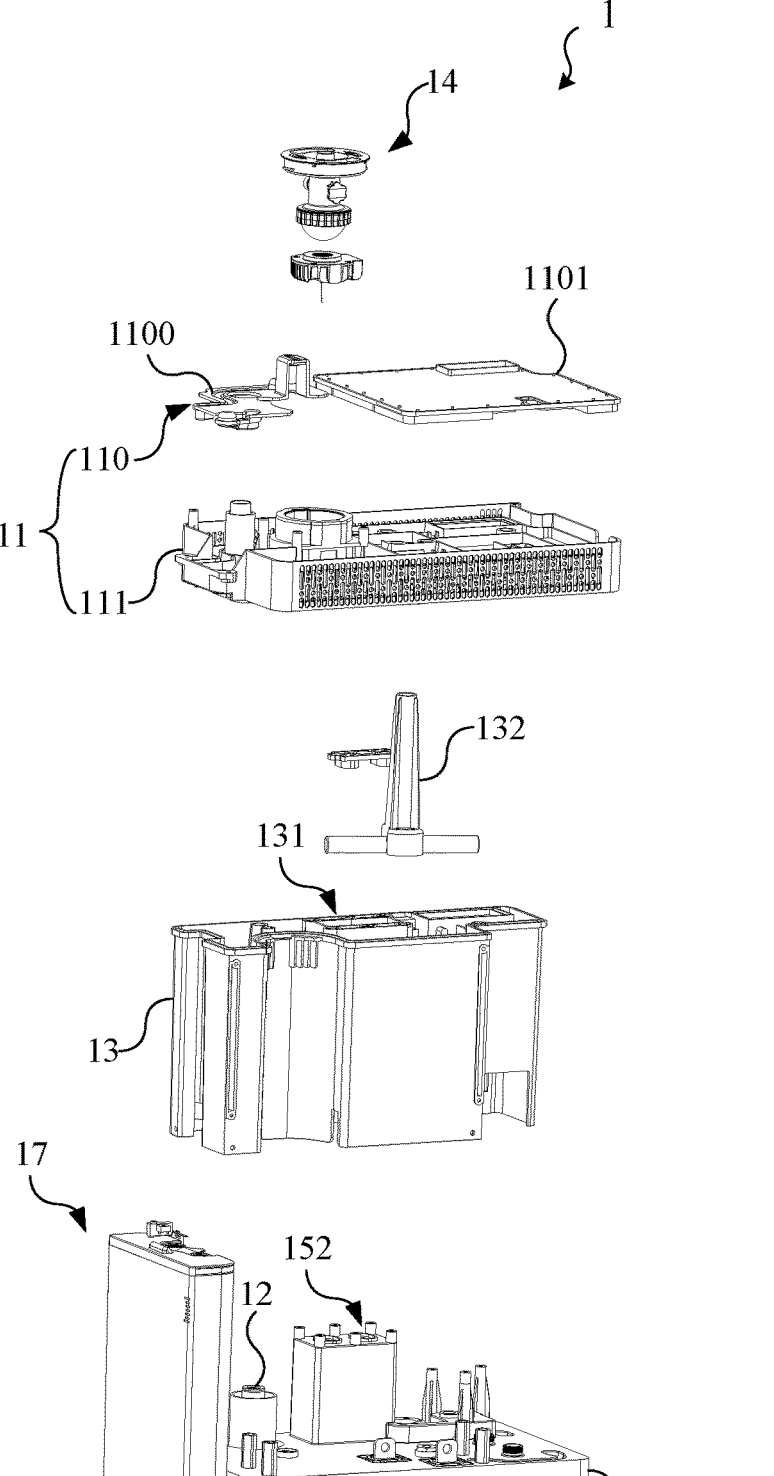
FIG. 9 is an exploded view of the structural diagram illustrating the hydrogen generating device of the breathing equipment according to another embodiment of the present invention.
Figure 10:
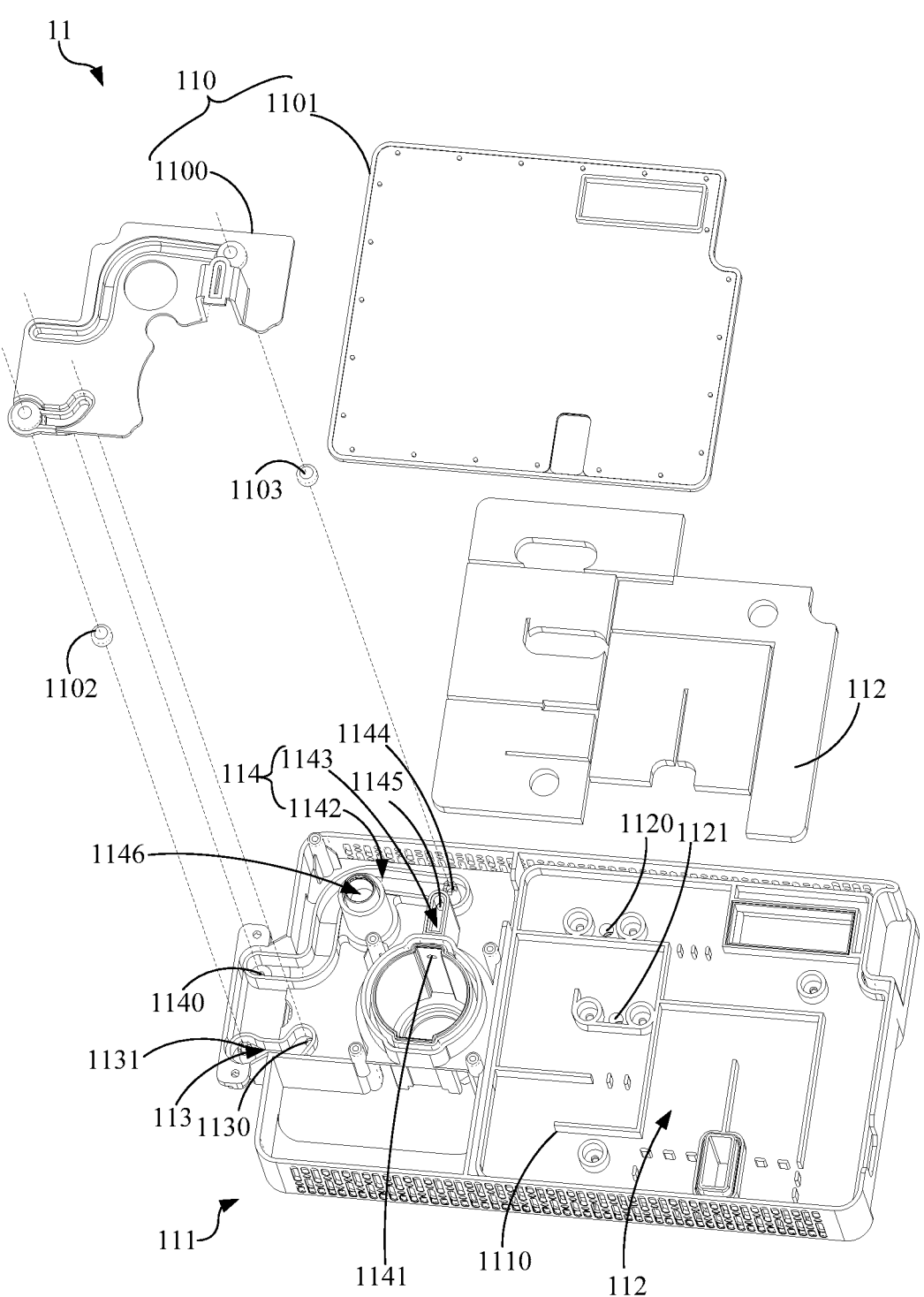
FIG. 10 is an exploded view of the structural diagram illustrating partial structure of the hydrogen generating device of the breathing equipment according to another embodiment of the present invention.
Figure 11A:
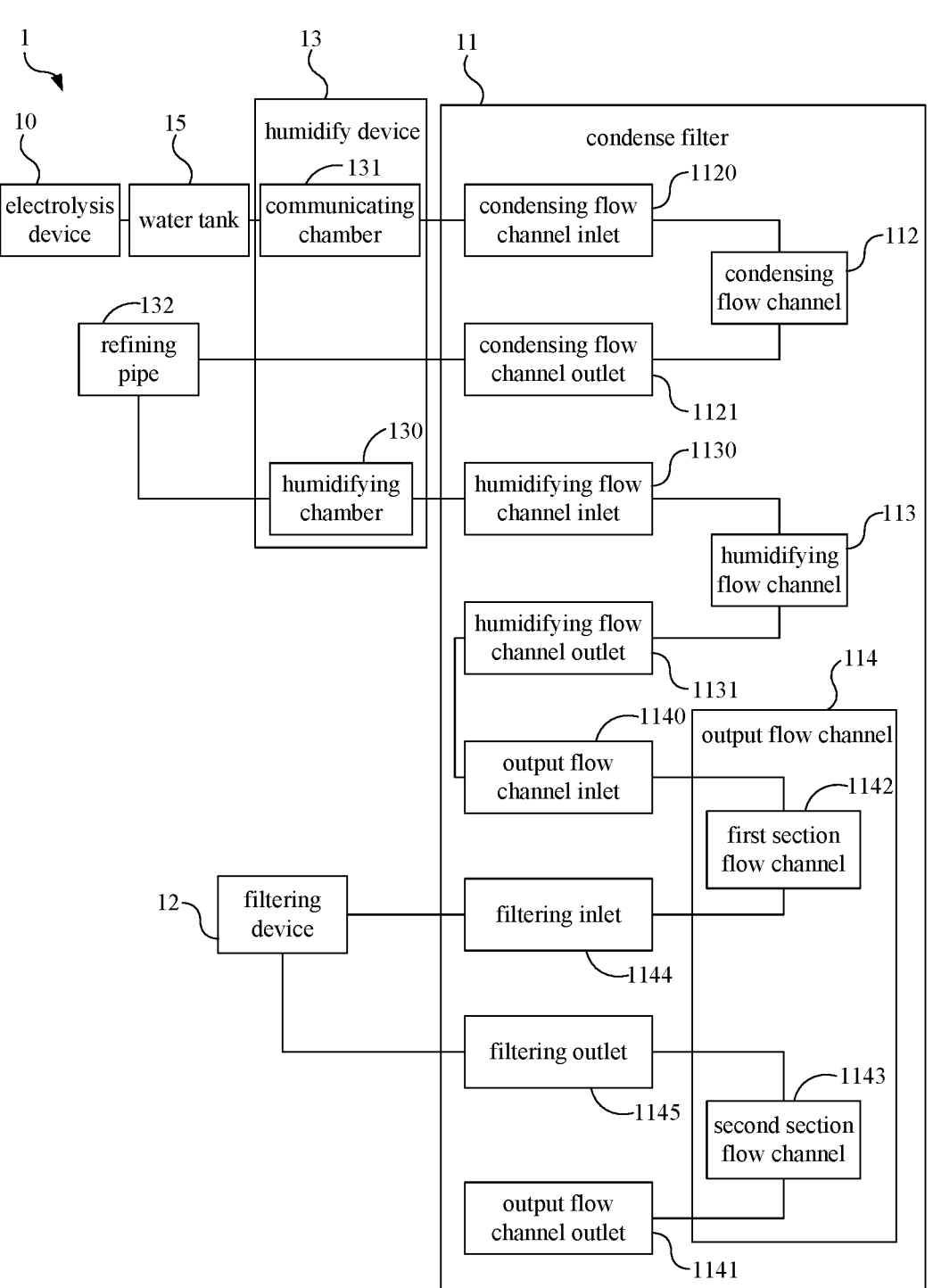
FIG. 11A is a function block diagram illustrating the hydrogen generating device of the breathing equipment according to another embodiment of the present invention.
Figure 11B:
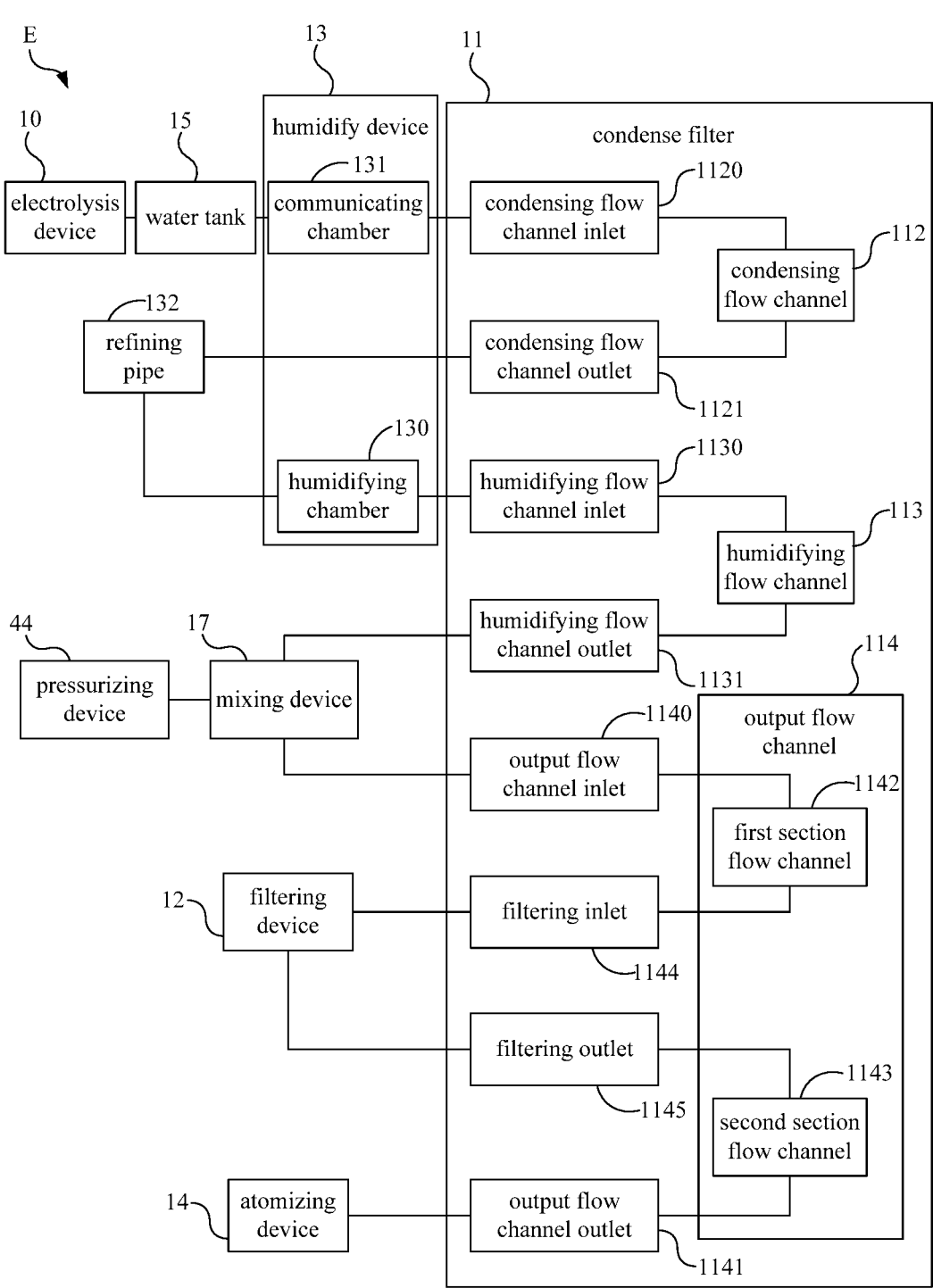
FIG. 11B is a function block diagram illustrating the breathing equipment according to another embodiment of the present invention.

Please refer to FIG. 9 to FIG. 11B. FIG. 9 is an exploded view of the structural diagram illustrating the hydrogen generating device 1 of the breathing equipment E according to another embodiment of the present invention. FIG. 10 is an exploded view of the structural diagram illustrating partial structure of the hydrogen generating device 1 of the breathing equipment E according to another embodiment of the present invention. FIG. 11A is a function block diagram illustrating the hydrogen generating device 1 of the breathing equipment E according to another embodiment of the present invention. FIG. 11B is a function block diagram illustrating the breathing equipment E according to another embodiment of the present invention. In a specific embodiment, the hydrogen generating device 1 comprises a water tank 15, the electrolysis device 10, the condense filter 11, the humidify device 13 and the atomizing device 14. The water tank 15 is configured to accommodate the water. The electrolysis device 10 is configured in the water tank, and is configured to electrolyze the water to generate the gas comprising hydrogen. The electrolysis device 10 may be an electrolysis device 10 of a non-ion membrane electrolysis device, which is composed of a combination of multiple electrode plates. The condense filter 11 is stacked above the water tank 15 and communicates with the water tank 15. The condense filter 11 comprises an integrated flow channel and a filtering material accommodated in the integrated flow channel. The filtering material of the condense filter is configured to filter out the electrolyte or impurities from the gas comprising hydrogen.

The hydrogen generating device 1 may additionally comprise a filtering device 12 to further filter out impurities (such as chlorine gas or electrolyte in the gas comprising hydrogen). In another embodiment, the filtering device 12 may comprise a conventional filter such as an activated carbon filter or an asbestos filter. Wherein, the hydrogen generating device 1 can be filtered by the condense filter 11 first, and then deeply filtered by the filtering device 12.

The humidify device 13 is stacked on the water tank 15 and communicates with the condense filter 11, and in one embodiment, the humidify device 13 is configured between the water tank 15 and the condense filter 11. The humidify device 13 has a humidifying chamber 130 and a communicating chamber 131. The humidifying chamber 130 can be configured to humidify the gas comprising hydrogen, and the communicating chamber 131 can be configured to communicate the water tank 15 and the condense filter 11, and the communicating chamber 131 is not connected to the humidifying chamber 130. In practical applications, the humidify device 13 can humidify the gas comprising hydrogen or obtain the gas comprising hydrogen humidified by pumping the gas comprising hydrogen into water, so as to avoid the user's airway drying caused by the inhalation of pure gas. In actual use, the humidify device 13 can drive the gas comprising hydrogen into the water contained in the humidifying chamber 130 through the thinning pipe 132 to obtain the gas comprising hydrogen humidified.

The atomizing device 14 can use an oscillator to selectively generate the atomizing gas from the liquid in an oscillating manner, and the atomizing gas is mixed with the gas comprising hydrogen to generate a health-care gas. The atomizing device 14 outputs the health-care gas to the output device 20, wherein the atomizing gas can be selected from at least one of water vapor, volatile essential oil, medicinal mist, and the like.

The gas comprising hydrogen generated by the electrolysis device 10 passes through the water tank 15 to the condense filter 11, the humidify device 13, and the atomizing device 14, and then is outputted to the breathing mask M1 by the output device 20 for inhalation by the user. In detail, in this embodiment, the water tank 15 comprises a cover 150 and a body 151. The body 151 can accommodate the water to be electrolyzed, and the cover 150 can cover the body 151. The electrolysis device 10 is configured in the water tank 15, and can receive the water to be electrolyzed from the water tank 15 and electrolyze it to generate the gas comprising hydrogen into the water tank 15. The condense filter 11, the filtering device 12, and the humidify device 13 are all vertically arranged on the water tank 15, and the vertical arrangement sequence among the condense filter 11, the filtering device 12 and the humidify device 13 can be interchanged.

As shown in FIG. 10, FIG. 11A and FIG. 11B, the integrated flow channel comprises an upper cover 110 and a lower cover 111. The upper cover 110 combines with the lower cover 111 to form a condensing flow channel 112, a humidifying flow channel 113 and an output flow channel 114, and the lower cover 111 is an integrally formed structure. Wherein, the lower cover 111 has a condensing flow channel inlet 1120 and a condensing flow channel outlet 1121 connected with the condensing flow channel 112, a humidifying flow channel inlet1 130 and a humidifying flow channel outlet 1131 connected with the humidifying flow channel 113, and an output flow channel inlet 1140 and an output flow channel outlet 1141 connected with the output flow channel 114. The condensing flow channel inlet 1120 is connected to the water tank 15 to receive the gas comprising hydrogen. The humidify device 13 is fitted with the lower cover 111 to respectively communicate with the condensing flow channel outlet 1121 and humidifying flow channel inlet 1130 to humidify the gas comprising hydrogen and send the gas comprising hydrogen to the humidifying flow channel 113.

As shown in FIG. 10, the upper cover 110 of the condense filter 11 may comprise a first upper cover 1100 and a second upper cover 1101. The first upper cover 1100 and the lower cover 111 may form the humidifying flow channel 113 and the output flow channel 114. The lower cover 111 has a plurality of spacing plates 1110 in a specific arrangement. When the second upper cover 1101 and the lower cover 111 are combined, the condensing flow channel 112 will be formed. The hydrogen generating device 1 further comprises the plurality of filtering material 117. The filtering material 117 may be configured in the condensing flow channel 112 to preliminarily filter out the impurities in the gas comprising hydrogen. The aforementioned spacing plates 1110 can be configured to separate the plurality of filtering material 117 to avoid overlapping of the filtering material 117, or to avoid the effect of condensation and moisture absorption reducing from the filtering material 117 contact each other.

The condense filter 11 can receive replenishing water to flush the electrolyte remaining in the filtering material 117 back to the water tank 15. Wherein, the humidify device 13 accommodates the replenishing water to humidify the gas comprising hydrogen, and can provide the replenishing water to pre-condensate the condense filter 11.

The hydrogen generating device 1 may further comprise the filtering device 12 coupled to the lower cover 111 for filtering out impurities from the gas comprising hydrogen. The lower cover 111 further comprises a filtering inlet 1144 and a filtering outlet 1145 to connect to the filtering device 12. The output flow channel 114 is divided into a first section flow channel 1142 and a second section flow channel 1143. The first section flow channel 1142 communicates with the output flow channel inlet 1140 and the filtering inlet 1144 to input the gas comprising hydrogen into the filtering device 12. The second section flow channel 1143 communicates with the filtering outlet 1145 and the output flow channel outlet 1141 to output the gas comprising hydrogen or the positive pressure gas from the filtering device 12.

The above-mentioned arrangement and functional design of the units in the vertically stacked hydrogen generating device 1, especially the integrated flow channel and the lower cover 111 integrally formed can not only reduce the volume of the device, but also reduce the problems of water leakage, air leakage and loose pipes caused by pipeline connections.

As shown in FIG. 11A and FIG. 11B, the embodiment of FIG. 11A is a hydrogen generating device 1 and the embodiment of FIG. 11B is the breathing equipment E which is an example of combining the hydrogen generating device 1 with the mixing device 17 and the atomizing device 14. In the embodiment of FIG. 11B, the mixing device 17 can be fitted into the lower cover 111 to communicate with the humidifying flow channel outlet 1131 and the output flow channel inlet 1140 respectively. The mixing device 17 is coupled to the pressurizing device 44. The pressurizing device 44 comprises the air compression device 440 or the high-pressure air cylinder 441 for accelerating the external gas to generate the accelerating gas. The mixing device 17 can be configured to mix the gas comprising hydrogen with the accelerating gas to generate the positive pressure gas. The atomizing device 14 can be fitted into the lower cover 111 to communicate with the output flow channel outlet 1141, so that the positive pressure gas is outputted from the output flow channel outlet 1141 and the atomizing gas generated by the atomizing device 14 are mixed and outputted.

In another specific embodiment, the mixing device 17 communicates with the output flow channel outlet 1141 to mix the accelerating gas outputted by the pressurizing device 44 and the gas comprising hydrogen outputted from the output flow channel outlet 1141 into the positive pressure gas to output. The atomizing device 14 can be coupled to the mixing device 17 to mix and output the atomizing gas generated by the atomizing device 14 with the positive pressure gas. In another specific embodiment, the atomizing device 14 can be fitted into the lower cover 111 to communicate with the output flow channel outlet 1141 to mix the atomizing gas generated by the atomizing device 14 with the gas comprising hydrogen outputted from the output flow channel outlet 1141. The mixing device 17 can be coupled to the atomizing gas to mix the accelerating gas outputted from the pressurizing device 44 with the gas comprising hydrogen and the atomizing gas outputted from the atomizing device 14 to output the atomizing gas and the positive pressure gas.

Please refer to FIG. 2 again. When the general breathing equipment continues to provide positive pressure gas to the user, the user is uncomfortable because the positive pressure gas is too dry. Therefore, in order to keep the user's respiratory tract moist, the present invention uses the humidify device 13 to generate the gas comprising hydrogen humidified on the one hand. On the other hand, the health-care gas atomized can be generated by the atomizing device 14 and then delivered to the output device 20, so as to solve the discomfort caused by the dry airway of the user caused by the continuous supply of the positive pressure gas via the conventional breathing equipment. Furthermore, the temperature of the positive pressure gas generated by the general breathing equipment is likely to be too low, causing discomfort to the user's trachea due to the low temperature. However, the gas comprising hydrogen generated by the water to be electrolyzed in the present invention generally has a temperature of about 30 to 60 degrees Celsius. The atomizing device 14 has a heating function (for example, the atomizing device 14 is an ultrasonic oscillator that increases the temperature of the atomizing gas when it oscillates and atomizes) to keep the atomizing gas at an appropriate temperature. Therefore, the temperature of the positive pressure gas mixed with the external air (such as the pressuring gas) will not be too low, so as to avoid the temperature of the positive pressure gas being too low and causing discomfort to the user's trachea due to the low temperature. Of course, an additional heating function can also be provided in the pressurizing device to increase the temperature of the accelerating gas or the pressuring gas.

However, the moisture provided by the humidify device 13 or the atomizing device 14 and the moisture generated by the user's own exhalation may cause the environment in the breathing mask M1 to be excessively humid, and make the user's breathing difficult. In order to solve the unsatisfactory breathing caused by the excessive humidity in the environment in the breathing mask M1, the breathing equipment E of the present invention further comprises the water vapor condensing pipe 5 communicated with the output device 20. The water vapor condensing pipe 5 can be configured to receive the positive pressure gas outputted by the output device 20. When the positive pressure gas is over-wet, the water vapor will stay in the water vapor condensing pipe 5. When there is too much condensed water in the water vapor condensing pipe 5, the water vapor condensing pipe 5 can also be disassembled to pour out the condensed water and be installed back again.

The breathing equipment E of the present invention can be connected to the breathing mask M1 from the output device 20 to provide the gas comprising hydrogen in the breathing equipment E for inhalation by the user wearing the breathing mask M1. Please refer to FIG. 12 and FIG. 13.

Figure 12:
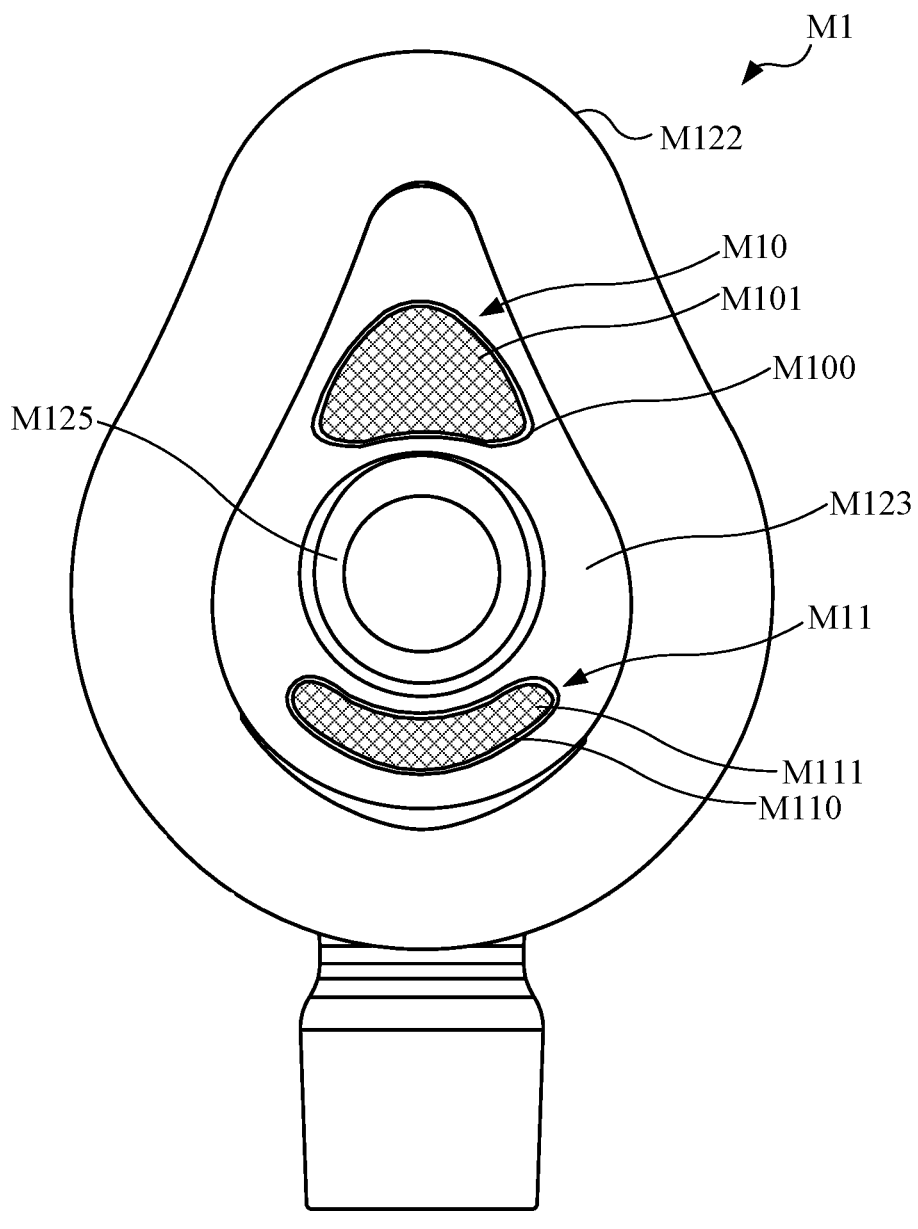
FIG. 12 is a function block diagram illustrating the breathing mask of the breathing equipment according to an embodiment of the present invention.
Figure 13:
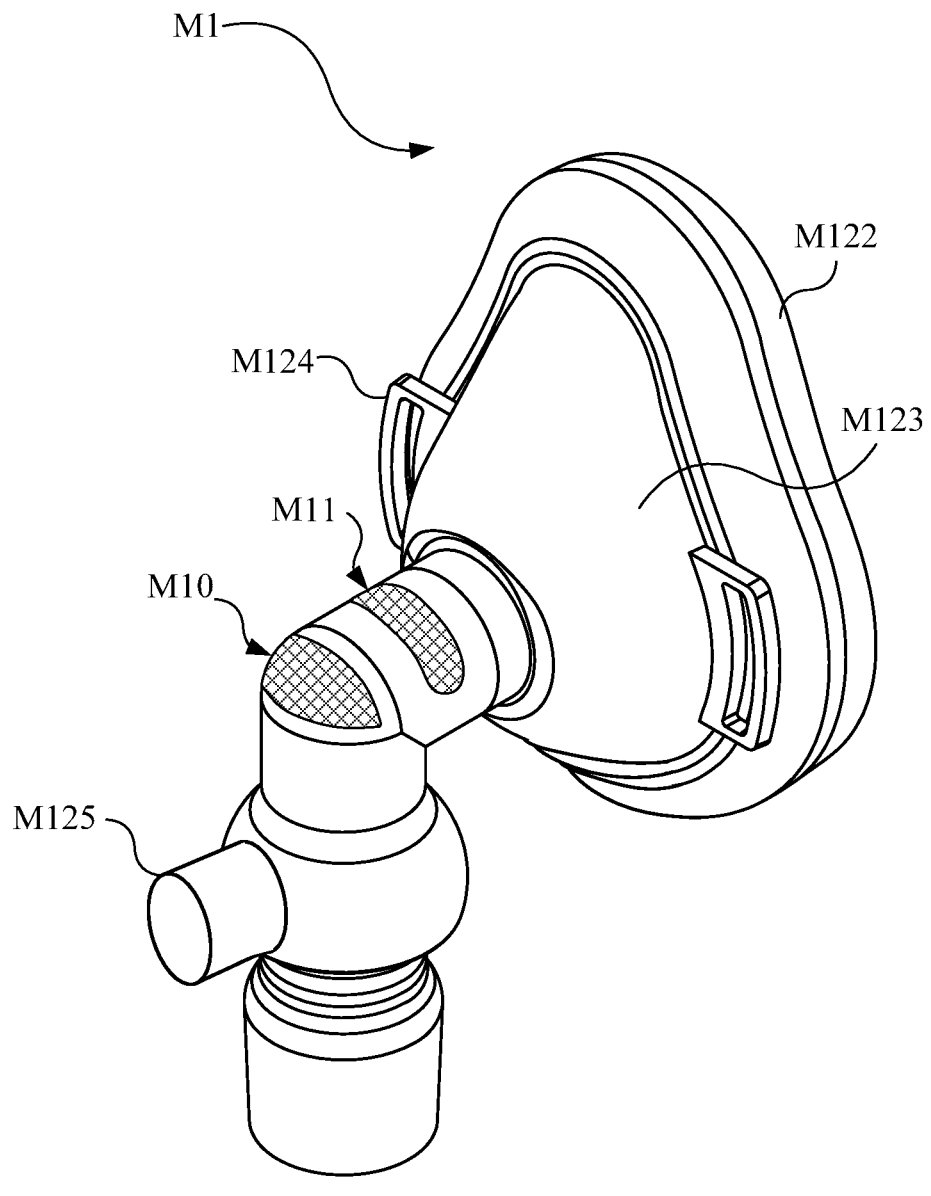
FIG. 13 is a schematic diagram illustrating the breathing mask from another perspective of the breathing equipment according to an embodiment of the present invention.

FIG. 12 is a function block diagram illustrating the breathing mask M1 of the breathing equipment E according to an embodiment of the present invention. FIG. 13 is a schematic diagram illustrating the breathing mask M1 from another perspective of the breathing equipment E according to an embodiment of the present invention. The breathing mask M1 comprises an air unidirectional entry unit M10, a gas unidirectional outgoing unit M11, an airtight structure M122, an air cavity structure M123, a positioning structure M124, and a connection port M125. The air unidirectional entry unit M10 comprises a gas inlet M100 and a mask first one-way valve M101 connected to the gas inlet M100, for allowing air in the external environment to unidirectionally enter the breathing mask M1. The gas unidirectional outgoing unit M11 comprises a gas outlet M110 and a mask second one-way valve M111 connected to the gas outlet M110 to allow the gas in the breathing mask M1 to unidirectionally flow out to the external environment. The airtight structure M122 is made of soft, flexible, and elastic materials, such as rubber, silicone, and foam. The airtight structure M122 can be configured to directly contact the user's skin and surround the user's airway entrance. The periphery of the air cavity structure M123 is connected with the airtight structure M122 to form a cavity for the user's mouth, nose, or mouth and nose to be placed, and the closed structure facilitates positive pressure air to enter the user's respiratory tract. The positioning structure M124 is configured on a side of the air cavity structure M123 away from the user. The positioning structure M124 can be used with a fixing device, such as a fixing belt, so that the breathing mask M1 can be stably maintained in a proper position during use. The connection port M125 connects the breathing mask M1 and the output device 20. In some embodiments, one or more of these features can be provided by one or more physical components. In some embodiments, a physical component can provide one or more functional characteristics.

The air unidirectional entry unit M10 of the breathing equipment E of the present invention is used as a protection mechanism. Under normal circumstances, since the inside of the breathing mask M1 is in a positive pressure environment, there will be no external gas entering the breathing mask M1 from the air unidirectional entry unit M10. However, if the inside of the breathing mask M1 is in an abnormal situation of a negative pressure environment, the external gas will enter the breathing mask M1 from the air unidirectional entry unit M10 to eliminate the negative pressure state.

The breathing mask M1 of the breathing equipment E of the present invention is designed to fit the face when in use. In a specific embodiment, the breathing mask M1 may be a nasal mask type that surrounds the two nostrils, a nasal pillow type that fits the left nostril and the right nostril respectively, a mask type that surrounds the mouth, or a full-face mask that surrounds the nose and mouth. The above-mentioned types of breathing mask M1 can be selected according to personal habits.

In a specific embodiment, the air unidirectional entry unit M10 and a gas unidirectional outgoing unit M11 may be disposed on the air cavity structure M123. In another specific embodiment, the air unidirectional entry unit M10 and the gas unidirectional outgoing unit M11 may be disposed on the connection port M125. Those skilled in the art can understand that the air unidirectional entry unit M10 and the gas unidirectional outgoing unit M11 can be installed anywhere on the breathing mask M1, and are not limited by the installation positions provided in the embodiments of this specification.

In a specific embodiment, the breathing equipment E of the present invention is a fixed pressure type positive pressure breathing device. The monitoring device 4 of the breathing equipment E can provide the gas comprising hydrogen with a fixed output volume and pressure according to the doctor's recommended pressure. The pressure of the gas comprising hydrogen only needs to be large enough to allow the patient's upper respiratory tract to be unblocked, so as to eliminate the breathing interruption, shallow breathing, breathing effort-related awakening, and snoring. It does not need to be too large to make users feel uncomfortable due to unnecessary pressure.

In another specific embodiment, the breathing equipment E of the present invention is an automatic positive pressure breathing device. The monitoring device 4 of the breathing equipment E automatically adjusts the delivery pressure according to the breathing status of the individual during sleep. Each person's upper airway pressure will have a different degree of relaxation due to the individual's different sleep stages. In addition, everyone's stress needs will also be affected by factors such as diet, medication and sleep environment, posture, lifestyle changes, weight at the time, and whether they are sick or not. Therefore, there may be different pressure requirements for everyday and every hour. In this embodiment, the breathing abnormality detector 3 is a pressure feedback sensing device. The pressure feedback sensing device detects the pressure change when the user breathes. When the breathing abnormality detector 3 senses that the user is in a normal breathing condition, the breathing equipment E will send out the gas comprising hydrogen at a pressure that does not affect the user's normal breathing. When the breathing abnormality detector 3 senses that the user is in a situation of stopping breathing, shallow breathing or snoring, the breathing equipment E will increase the pressure of the gas comprising hydrogen to allow the user to resume breathing. In a specific embodiment, the breathing abnormality detector 3 can estimate the user's respiratory condition by sensing the output of the gas comprising hydrogen in the output device 20. When the output device 20 cannot smoothly output the gas comprising hydrogen, it can be inferred that the user is in the abnormal breathing condition. Otherwise, it is assumed that the user is in a normal breathing condition.

In more another specific embodiment, the breathing equipment E of the present invention can be manually adjusted to the fixed pressure type or the automatic type as described above, so as to achieve personalized settings. It does not limit the breathing equipment E of the present invention to only one of the present modes.

In a specific embodiment, the hydrogen generating device 1 is coupled to the respiratory abnormality detector 3 to receive the signal generated by the breathing abnormality detector 3, and starts electrolyzing water according to the signal to generate the gas comprising hydrogen. When the breathing equipment E is in the normal breathing state, the user can use the air unidirectional entry unit M10 and the gas unidirectional outgoing unit M11 on the breathing mask M1 to perform normal breathing. When it is detected that the user is in the breathing stop, shallow breathing or snoring situation, the hydrogen generating device 1 is then activated to deliver the gas comprising hydrogen for the user to inhale. In practical applications, the breathing abnormality detector 3 can detect the user's exhalation and inhalation pressure and the interval time. When the breathing abnormality detector 3 detects the user's inhalation, but does not detect the pressure difference inside the breathing mask M1 caused by the corresponding user's inhalation, the breathing abnormality detector 3 will find the positive pressure value which the user's airway can be opened by the positive pressure gas based on the upper and lower pressure values that the breathing equipment E can reach. In another practical application, the user can set a preset period of time so that the respiratory pressure value will not be changed when the user has not fallen asleep; but after the user has fallen asleep, the breathing abnormality detector 3 will start to detect abnormal breathing to assist the user's breathing during sleep.

Please refer to FIG. 1 again. In practical applications, the breathing equipment E of the present invention can provide the following 4 modes for users to choose from. The first mode is a built-in mode, which has at least one use parameter pre-stored, and its use parameters include use parameters recommended by doctors for ordinary users, use parameters recommended by doctors for users with specific symptoms, or commonly used use parameters. When the user selects at least one use parameter of this built-in mode, the monitoring device 4 will adjust the pressure, the gas composition, the gas concentration, etc., inside the breathing mask M1 according to the selected built-in mode. Wherein, the monitoring device 4 uses the flow control unit 40, the air compression device 440 or the high-pressure air cylinder 441 to adjust the pressure, gas composition, and gas concentration inside the breathing mask M1. The second mode is to adjust the pressure, the gas composition, the gas concentration, etc., inside the breathing mask M1 with the breathing adjustment parameters required by the medical staff to provide for the user. The breathing equipment E of the present invention further comprises a transmission device 6 coupled with the monitoring device 4, and the user or medical staff can use wireless transmission such as Wi-Fi, local area network, Bluetooth or infrared transmission or wired transmission way to transmit this breathing adjustment parameter to the transmission device 6. The monitoring device 4 will adjust the pressure, the gas composition, the gas concentration, etc., inside the breathing mask M1 according to the breathing adjustment parameters received by the transmission device 6. In other words, the breathing equipment E can be set by using external parameter files containing the breathing adjustment parameters. The third mode is the manual input mode. The monitoring device 4 of the breathing equipment E of the present invention can be further coupled with a terminal device 7. The user or medical staff can set the breathing adjustment parameters through the terminal device 7. The monitoring device 4 may directly receive the breathing adjustment parameter set by the terminal device 7 or the transmission device 6 may receive the breathing adjustment parameter and then transmit it to the monitoring device 4. The monitoring device 4 will adjust the pressure, the gas composition, the gas concentration, etc., inside the breathing mask M1 according to the breathing adjustment parameters. The fourth mode is the smart mode. In a specific embodiment, the breathing abnormality detector 3 is a wearable device worn on the user. This wearable device detects the user's movement, heartbeat, blood oxygen concentration, and blood perfusion index to confirm whether the user is in the condition of stopping breathing, shallow breathing or snoring, and then generates a signal. The monitoring device 4 will adjust the pressure output to the external environment according to this signal.

In addition to the breathing equipment E mentioned above, the present invention also provides the breathing equipment E, which comprises the hydrogen generating device 1, the output device 20, and the monitoring device 4. Wherein, the hydrogen generating device 1 and the output device 20 are the same as the aforementioned breathing equipment E, and will not be repeated here. The monitoring device 4 is coupled to at least one of the hydrogen generating device 1 and the output device 20. The monitoring device 4 is configured to adjust the pressure of the gas output to the external environment according to the breathing adjustment parameters.

When the monitoring device 4 is coupled to the hydrogen generating device 1, the monitoring device 4 can adjust at least one of the rate at which the hydrogen generating device 1 generates the gas comprising hydrogen and the flow rate of the gas comprising hydrogen flowing from the hydrogen generating device 1 to the output device 20 according to the breathing adjustment parameters for adjusting the pressure of the gas output to the external environment. When the monitoring device 4 is coupled to the output device 20, the monitoring device 4 can adjust the flow rate of the gas comprising hydrogen to the output device 20 according to the breathing adjustment parameter, thereby adjusting the pressure of the gas output to the external environment.

In practical applications, the breathing mask M1 can be connected to the output device 20 to receive the gas comprising hydrogen. Therefore, the breathing equipment E can further adjust the internal pressure of the gas in the breathing mask M1. In addition to providing the gas comprising hydrogen, the monitoring device 4 of the present invention further comprises the air compression device 440 connected to the output device 20, and the air compression device 440 can be configured to inhale and compress air from the external environment. The monitoring device 4 provides the compressed air to the output device 20 according to the breathing adjustment parameters, thereby adjusting the pressure of the gas in the breathing mask M1. In addition, the monitoring device 4 of the present invention may further comprise the high-pressure air cylinder 441 connected to the output device 20. The high-pressure air cylinder 441 stores the high-pressure air. The monitoring device 4 provides the high-pressure air in the high-pressure air cylinder 441 to the output device 20 according to the breathing adjustment parameters, thereby adjusting the pressure of the gas inside the breathing mask M1.

In a specific embodiment, the breathing adjustment parameter may be the user's breathing frequency by detection, the positive pressure gas (or mixed with the atomizing gas) is outputted during inhalation, and the gas comprising hydrogen (or mixed with the atomizing gas) is outputted during exhalation. In another embodiment, the positive pressure gas (or mixed with atomizing gas) with a higher pressure is outputted during inhalation, and a positive pressure gas with a lower pressure (or mixed with atomized gas) is outputted during exhalation. Namely, the monitoring device 4 can periodically generate the positive pressure gas according to the user's breathing frequency.

The breathing equipment E can be configured for mild patients or users who perform breathing assistance with a fixed pressure value. In practical applications, the user can turn on the breathing equipment E and start to sleep. After a preset period of time, the breathing equipment E will start electrolysis with the set breathing adjustment parameters and provide the gas comprising hydrogen with positive pressure for the user. The preset time can be set by the user or be the built-in time of the breathing equipment E itself.

According to relevant medical data, during normal sleep, an adult breathes approximately 16-20 times per minute, and the average flow rate per breath is 4-10 liters/minute (the actual value depends on each person's vital capacity). During breathing, the peak inspiratory pressure of an adult is 10-20 cm-$H_2O$ (depending on the individual, the minimum can be 2~5 cm-$H_2O$ and the maximum can be 30 cm-$H_2O$). For patients with lung disease, different degrees of lung disease also have different peaks of inspiratory pressure. Mild lung disease is 20~25 cm-$H_2O$; moderate lung disease is 25~30 cm-$H_2O$; severe lung disease is higher than 30 cm-$H_2O$, and if you have respiratory distress syndrome (Respiratory Distress Syndrome, RDS) and pulmonary hemorrhage can be as high as 60 cm-$H_2O$. According to this medical data, the breathing equipment E of the present invention can provide a total gas production of 10-12 L/min, wherein the hydrogen production is about 3.0-4.5 L/min for the user to perform positive pressure breathing therapy. The breathing equipment E of the present invention can provide a minimum of 2 cm-$H_2O$ and a maximum of 70 cm-$H_2O$ for users to choose. The breathing equipment E of the present invention can provide users with different pressure range settings, such as: single range setting:2~25 cm-$H_2O$, 3~20 cm-$H_2O$, 3~25 cm-$H_2O$, 3~33 cm-$H_2O$, 4~20 cm-$H_2O$, 4~35 cm-$H_2O$, 5~18 cm-$H_2O$, 5~20 cm-$H_2O$, 5~33 cm-$H_2O$, 5~60 cm-$H_2O$, 6~50 cm-$H_2O$, or set the highest value 35 cm-$H_2O$ or 30 cm-$H_2O$. The setting of the plural range: inhalation is 3~30 cm-$H_2O$, exhalation is 3~20 cm-$H_2O$. The inspiratory frequency range is 4~40 cm-$H_2O$ or 5~30 cm-$H_2O$. The suction pressure range can be 4~30 cm-$H_2O$, 4~40 cm-$H_2O$, 3~30 cm-$H_2O$ or the highest value 20 cm-$H_2O$. The breathing pressure range can be 2~30 cm-$H_2O$, 2~40 cm-$H_2O$ or 3~20 cm-$H_2O$. As long as the set range is within the feasible range of the breathing equipment E of the present invention, the user can set it according to the doctor's suggestion or personal preferences to achieve the best and most comfortable treatment effect. In addition, the breathing equipment E of the present invention can be used continuously for 12 hours, the power is less than 1000 W, and the atomization volume is greater than 30 mL.

In practical applications, the breathing equipment E of the present invention can monitor high pressure, low pressure, low pressure delay, apnea, low minute ventilation, high and low breathing frequency, peak flow description, and air leakage. In the range of 0~2438 meters above sea level, the pressure change caused by the altitude will be automatically compensated by the breathing equipment E of the present invention. In the range of 5° C. to 45° C., pressure fluctuations caused by temperature changes will be automatically compensated by the breathing equipment E of the present invention and the automatic air leakage compensation can reach up to 60 L/min.

In a specific embodiment, the breathing equipment E of the present invention is not limited to patients with respiratory arrest, and can also be provided to patients with respiratory disorders such as Chen-Shi breathing, obesity hypoventilation syndrome, chronic obstructive pulmonary disease and the like.

Compared with the prior art, the breathing equipment E of the present invention provides positive pressure gas to the user, and also allows the user to inhale the gas comprising hydrogen or the health-care gas. Therefore, the breathing equipment E of the present invention can assist the daily treatment of patients with sleep apnea and other respiratory disorders. The breathing equipment E is also possible to provide users with the gas comprising hydrogen and the health-care gas, so that users who use the breathing equipment E for a long time can alleviate the oxidative damage that may be caused by positive pressure ventilation. This oxidative damage is caused by the breathing equipment that continuously provides excess gas at the positive pressure for the user to inhale, and then causes the user to breathe the excess gas. Excessive breathing of gas will cause the user's body to expand the alveoli, run into the gastrointestinal tract, and enter the body space due to the unnecessary excess gas. In turn, the user's body is exposed to oxidative damage caused by the oxygen contained in a lot of excess gas. The breathing equipment E of the present invention adds the gas comprising hydrogen and the health-care gas to the positive pressure gas, thereby combining with the oxygen in the excess gas to form water and health care of damaged body parts, and then achieving the effects of anti-oxidation, anti-aging, eliminating chronic diseases and beauty and health care.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A breathing equipment for providing positive pressure gas, comprising: a gas channel; a hydrogen generating device coupled to the gas channel and configured to electrolyze water to generate a gas comprising hydrogen; a pressurizing device coupled to the gas channel and configured to selectively accelerate an external gas to generate an accelerating gas; a mixing device coupled to the gas channel and configured to mix the gas comprising hydrogen and the accelerating gas to generate the positive pressure gas; and an output device coupled to the gas channel and configured to selectively output the gas comprising hydrogen or the positive pressure gas;

wherein the hydrogen generating device further comprises:

a water tank configured to accommodate the water; an electrolysis device configured in the water tank, and configured to electrolyze the water to generate the gas comprising hydrogen; a condensing filter comprising an integrated flow channel and a filtering material configured to be in the integrated flow channel, the filtering material of the condensing filter being configured to filter out an electrolyte from the gas comprising hydrogen, wherein the condensing filter receives replenishing water to flush the electrolyte remaining in the filtering material back to the water tank; and a humidifing device configured to accommodate the replenishing water for humidifying the gas comprising hydrogen, and provide the replenishing water to the condense filter; wherein the integrated flow channel comprises an upper cover and a lower cover, the upper cover combines with the lower cover to form a condensing flow channel, a humidifying flow channel and an output flow channel, and the lower cover is an integrally formed structure, wherein the lower cover has a condensing flow channel inlet and a condensing flow channel outlet connected with the condensing flow channel, a humidifying flow channel inlet and a humidifying flow channel outlet connected with the humidifying flow channel, and an output flow channel inlet and an output flow channel outlet connected with the output flow channel; wherein the humidifing device is embedded with the lower cover to communicate with the condensing flow channel outlet and humidifying flow channel inlet, the humidifing device is configured to humidify the gas comprising hydrogen and send the gas comprising hydrogen to the humidifying flow channel; the humidifing device comprises a humidifying chamber and a communicating chamber, the humidifying chamber is configured to humidify the gas comprising hydrogen, the communicating chamber is configured to communicate the water tank and the condensing filter, and the communicating chamber does not communicate with the humidifying chamber.

2. The breathing equipment of claim 1, further comprising:

a breathing abnormality detector coupled to the gas channel and configured for detecting whether a breathing abnormality occurs on a user who uses the breathing equipment and selectively generating an abnormal signal; and a monitoring device coupled to the breathing abnormality detector, and configured for activating the pressurizing device to generate the accelerating gas according to the abnormal signal.

3. The breathing equipment of claim 1, wherein when the monitoring device activates the pressurizing device, the output device outputs the positive pressure gas; when the monitoring device does not activate the pressurizing device, the output device outputs the gas comprising hydrogen.

4. The breathing equipment of claim 3, further comprising an atomizing device and an atomizing device switch, wherein the atomizing device is coupled to the gas channel and configured to selectively generate an atomizing gas, and the output device is configured to selectively output the gas comprising hydrogen, the positive pressure gas, the gas comprising hydrogen with the atomizing gas, or the positive pressure gas with the atomizing gas, when the monitoring device activates the pressurizing device and the atomizing device switch, the output device outputs the positive pressure gas with the atomizing gas; when the monitoring device does not activate the pressurizing device but activates the atomizing device switch, the output device outputs the gas comprising hydrogen with the atomizing gas.

5. The breathing equipment of claim 2, wherein the pressurizing device further comprises:

a filter configured to filter out the impurities in the external gas;

a fan device coupled to the filter, and configured to accelerate the external air after filtered to generate the accelerating gas; and a first flow sensor coupled to the fan device, and configured to detect the flow rate of the accelerating gas and transmit the value of the flow rate to the monitoring device.

6. The breathing equipment of claim 2, further comprising:

a first one-way valve and a first flame arrestor configured between the hydrogen generating device and the mixing device;

a second flame arrestor configured between the output device and the mixing device; and a second one-way valve configured between the pressurizing device and the mixing device.

7. The breathing equipment of claim 1, further comprising:

a trigger switch configured for a user to choose whether to activate the pressurizing device and selectively generate a trigger signal; and a monitoring device coupled to the trigger switch and configured for activating the pressurizing device to generate the accelerating gas according to the trigger signal.

8. The breathing equipment of claim 1, further comprising a transmission device coupled with a monitoring device, the transmission device being configured to receive a breathing adjustment parameter and transmit it to the monitoring device, and the monitoring device being configured to receive the breathing adjustment parameter and selectively adjust the flow rate of the accelerating gas according to the breathing adjustment parameter.

9. The breathing equipment of claim 4, further comprising a water vapor condensing pipe coupled to the output device, and the water vapor condensing pipe being configured to condense the water from a gas outputted by the output device, the gas being the gas comprising hydrogen, the positive pressure gas, the gas comprising hydrogen with the atomizing gas, or the positive pressure gas with the atomizing gas.

10. The breathing equipment of claim 1, wherein the condensing flow channel inlet communicates with the water tank to receive the gas comprising hydrogen, and the filtering material is configured in the condensing flow channel.

11. The breathing equipment of claim 1, further comprising an atomizing device and an atomizing device switch, wherein the atomizing device is coupled to the gas channel and configured to selectively generate an atomizing gas, and the output device is configured to selectively output the gas comprising hydrogen, the positive pressure gas, the gas comprising hydrogen with the atomizing gas, or the positive pressure gas with the atomizing gas, wherein the atomizing device is coupled to the output flow channel outlet.

12. The breathing equipment of claim 1, wherein the pressurizing device selectively generates the accelerating gas according to a breath status of a user, such that a gas pressure of the output device is changed over time.

13. The breathing equipment of claim 1, wherein the hydrogen generating device further comprises an expanded ion-exchange membrane electrolysis device, the expanded ion-exchange membrane electrolysis device comprises:

an anode plate:

a cathode plate:

a first bipolar electrode plate configured between the anode plate and the cathode plate, wherein a first ion-exchange membrane plate is accommodated between the anode plate and the first bipolar electrode plate, and a second ion-exchange membrane plate is accommodated between the cathode plate and the first bipolar electrode plate;

a first oxygen chamber adjacent to the anode plate, a first hydrogen chamber adjacent to the cathode plate, a second oxygen chamber adjacent to an anode surface of the first bipolar electrode plate, and a second hydrogen chamber adjacent to a cathode surface of the first bipolar electrode plate; wherein the first oxygen chamber communicates with the second oxygen chamber through an oxygen outlet channel, and the first hydrogen chamber communicates with the second hydrogen chamber through a hydrogen outlet channel; and a second bipolar electrode plate configured between the anode plate and the cathode plate, wherein a third oxygen chamber is adjacent to an anode surface of the second bipolar electrode plate, and a third hydrogen chamber is adjacent to a cathode surface of the second bipolar electrode plate;

wherein the third oxygen chamber communicates with the first oxygen chamber and the second oxygen chamber through the oxygen outlet channel, and the third hydrogen chamber communicates with the first hydrogen chamber and the second hydrogen chamber through the hydrogen outlet channel.

14. The breathing equipment of claim 13, wherein the expanded ion-exchange membrane electrolysis device further comprises an oxygen conduit and a hydrogen conduit, wherein the oxygen outlet channel penetrates the cathode plate or the anode plate to connect to the oxygen conduit, and the hydrogen outlet channel penetrates the cathode plate or the anode plate to connect to the hydrogen conduit.

15. A breathing equipment for providing a positive pressure gas, comprising: a gas channel; a hydrogen generating device coupled to the gas channel and configured to electrolyze water to generate a gas comprising hydrogen and oxygen; a pressurizing device coupled to the gas channel and configured to selectively accelerate an external gas to generate an accelerating gas; a monitoring device coupled to the pressurizing device, and configured to detect a gas signal to control the pressurizing device to generate the accelerating gas; a mixing device coupled to the gas channel and configured to mix the gas comprising hydrogen and oxygen with the accelerating gas to generate a positive pressure gas; and an atomizing device coupled to the gas channel and configured to selectively generate an atomizing gas to be mixed with the positive pressure gas; wherein the hydrogen generating device further comprises: a water tank configured to accommodate the water; an electrolysis device configured in the water tank, and configured to electrolyze the water to generate the gas comprising hydrogen and oxygen; a condensing filter comprising an integrated flow channel and a filtering material configured to be in the integrated flow channel, the filtering material of the condensing filter being configured to filter out an electrolyte from the gas comprising hydrogen and oxygen; and a humidifing device configured to accommodate replenishing water for humidifying the gas comprising hydrogen and oxygen; wherein the condensing filter receives the replenishing water from the humidify device to flush the electrolyte filtered by the condensing filter back to the water tank; wherein the integrated flow channel comprises an upper cover and a lower cover, the upper cover combines with the lower cover to form a condensing flow channel, a humidifying flow channel and an output flow channel, and the lower cover is an integrally formed structure, wherein the lower cover has a condensing flow channel inlet and a condensing flow channel outlet connected with the condensing flow channel, a humidifying flow channel inlet and a humidifying flow channel outlet connected with the humidifying flow channel, and an output flow channel inlet and an output flow channel outlet connected with the output flow channel; the condensing flow channel inlet is connected to the water tank to receive the gas comprising hydrogen and oxygen; the humidifing device is embedded with the lower cover to respectively communicate with the condensing flow channel outlet and humidifying flow channel inlet to humidify the gas comprising hydrogen and oxygen and send the gas comprising hydrogen and oxygen to the humidifying flow channel.

16. The breathing equipment of claim 15, wherein the monitoring device is configured to sense a breathing frequency of a user, and the breathing equipment periodically generates the positive pressure gas based on the breathing frequency.

17. The breathing equipment of claim 15, further comprising:
   a first one-way valve and a first flame arrestor configured between the hydrogen generating device and the mixing device;
   a second flame arrestor configured between the output device and the mixing device; and
   a second one-way valve configured between the pressurizing device and the mixing device.

18. The breathing equipment of claim 15, wherein the atomizing device or the pressurizing device has a heating function, to raise the temperature of the atomizing gas or the accelerating gas.

* * * * *